(12) United States Patent
Gazit et al.

(10) Patent No.: US 7,504,383 B2
(45) Date of Patent: Mar. 17, 2009

(54) PEPTIDE NANOSTRUCTURES ENCAPSULATING A FOREIGN MATERIAL AND METHOD OF MANUFACTURING SAME

(75) Inventors: Ehud Gazit, Ramat Hasharon (IL); Meital Reches, RaAnana (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 56 days.

(21) Appl. No.: 11/148,266

(22) Filed: Jun. 9, 2005

(65) Prior Publication Data

US 2006/0079455 A1   Apr. 13, 2006

Related U.S. Application Data

(63) Continuation-in-part of application No. PCT/IL2004/000012, filed on Jan. 7, 2004.

(60) Provisional application No. 60/458,378, filed on Mar. 31, 2003, provisional application No. 60/438,331, filed on Jan. 7, 2003.

(51) Int. Cl.
*A61K 38/00* (2006.01)
*C07K 2/00* (2006.01)
*C07K 4/00* (2006.01)

(52) U.S. Cl. ............... 514/19; 530/300; 530/330
(58) Field of Classification Search ............ None
See application file for complete search history.

(56) References Cited

U.S. PATENT DOCUMENTS

| | | | |
|---|---|---|---|
| 3,976,639 A | 8/1976 | Batcho et al. | |
| 4,299,917 A | 11/1981 | Berger et al. | |
| 4,331,647 A | 5/1982 | Goldenberg | |
| 4,925,673 A | 5/1990 | Steiner et al. | |
| 5,013,556 A | 5/1991 | Woodle et al. | |
| 5,270,163 A | 12/1993 | Gold et al. | |
| 5,304,470 A | 4/1994 | Fischer et al. | |
| 5,332,648 A | 7/1994 | Kihara et al. | |
| 5,475,096 A | 12/1995 | Gold et al. | |
| 5,556,744 A | 9/1996 | Weiner et al. | |
| 5,567,588 A | 10/1996 | Gold et al. | |
| 5,595,877 A | 1/1997 | Gold et al. | |
| 5,637,459 A | 6/1997 | Burke et al. | |
| 5,643,768 A | 7/1997 | Kawasaki | |
| 5,658,754 A | 8/1997 | Kawasaki | |
| 5,683,867 A | 11/1997 | Biesecker et al. | |
| 5,705,337 A | 1/1998 | Gold et al. | |
| 5,916,642 A | 6/1999 | Chang | |
| 6,162,828 A | 12/2000 | Fukuda et al. | |
| 6,251,625 B1 | 7/2001 | Bommarius et al. | |
| 6,261,569 B1 | 7/2001 | Comis et al. | |
| 6,309,669 B1 | 10/2001 | Setterstrom et al. | |
| 6,326,174 B1 | 12/2001 | Joyce et al. | |
| 6,359,112 B2 | 3/2002 | Kapurniotu et al. | |
| 6,361,861 B2 | 3/2002 | Gao et al. | |
| 6,610,478 B1 | 8/2003 | Takle et al. | |
| 6,613,875 B1 * | 9/2003 | Ghadiri | 530/321 |
| 6,617,114 B1 | 9/2003 | Fowlkes et al. | |
| 6,677,153 B2 | 1/2004 | Iversen | |
| 6,689,753 B1 | 2/2004 | Soto-Jara | |
| 6,858,318 B2 * | 2/2005 | Kogiso et al. | 428/606 |
| 6,976,639 B2 | 12/2005 | Williams et al. | |
| 2002/0006954 A1 | 1/2002 | Hensley et al. | |
| 2003/0130484 A1 | 7/2003 | Gordon et al. | |
| 2003/0158237 A1 | 8/2003 | Saragovi et al. | |
| 2005/0069950 A1 | 3/2005 | Haynie | |
| 2006/0234947 A1 | 10/2006 | Gazit | |
| 2007/0021345 A1 | 1/2007 | Gazit | |
| 2007/0135334 A1 | 6/2007 | Gazit | |

FOREIGN PATENT DOCUMENTS

| | | |
|---|---|---|
| DE | 3412445 | 10/1985 |
| DE | 10043282 | 3/2002 |
| EP | 0081122 | 6/1983 |
| EP | 0421946 | 4/1991 |
| EP | 966975 | 7/2005 |
| JP | 59-044313 | 3/1984 |
| JP | 60-040061 | 2/1985 |
| JP | 63-044895 | 2/1988 |
| JP | 02-295923 | 6/1990 |
| JP | 10-245342 | 9/1998 |
| JP | 2000-193661 | 7/2000 |
| WO | WO 80/00789 | 1/1980 |
| WO | WO 92/19253 | 11/1992 |
| WO | WO 97/16191 | 9/1997 |
| WO | WO 98/20135 | 5/1998 |

(Continued)

OTHER PUBLICATIONS

Clark et al. Self-Assembling Cyclic B3-Peptide Nanotubes as Artificial Transmembrane Ion Channels. JACS. 1998. vol. 120, pp. 651-656.*

Hartgerink et al. "Self-Assembling Peptide Nanotubes", Journal of the American Chemical Society, 118: 43-50, 1996.

Ajayan et al. "Applications of Carbon Nanotubes", Topics of Applied Physics, 80: 391-425, 2001.

Görbitz "Nanotube Formation by Hydrophobic Dipeptides", Chemistry, 7(23): 5153-5159, 2001.

Reches et al. "Amyloid Fibril Formation by Pentapeptide and Tetrapeptide Fragments of Human Calcitonin", Journal of Biological Chemistry, 277(38): 35475-35480, 2002.

Haldar et al. "First Crystallographic Signature of the Highly Ordered Supramolecular Helical Assemblage From A Tripeptide Containing A Non-Coded Amino Acid", Tetrahedron Letters, 43(14): 2653-2656, 2002.

(Continued)

*Primary Examiner*—Andrew D. Kosar
*Assistant Examiner*—Marcela M Cordero Garcia

(57) ABSTRACT

A composition comprising a material at least partially enclosed by a tubular, spherical or planar nanostructure composed of a plurality of peptides, wherein each of the plurality of peptides includes no more than 4 amino acids and whereas at least one of the 4 amino acids is an aromatic amino acid.

14 Claims, 18 Drawing Sheets
(1 of 18 Drawing Sheet(s) Filed in Color)

FOREIGN PATENT DOCUMENTS

| WO | WO 99/42102 | 8/1999 |
|---|---|---|
| WO | WO 99/58652 | 11/1999 |
| WO | WO 00/24390 | 4/2000 |
| WO | WO 01/10457 | 2/2001 |
| WO | WO 01/45726 | 6/2001 |
| WO | WO 01/49307 | 7/2001 |
| WO | WO 01/93836 | 12/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 7/2003 |
| WO | WO 03/070269 | 8/2003 |
| WO | WO 03/077866 | 9/2003 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 7/2005 |
| WO | WO 2007/029003 | 3/2007 |
| WO | WO 2007/043048 | 4/2007 |
| WO | WO 01/49281 | 7/2007 |

OTHER PUBLICATIONS

Maji et al. "Fibril-Forming Model Synthetic Peptides Containing 3-Aminophenylacetic Acid", Tetrahedron, 58(43): 8695-8702, 2002.
Hartgerink et al. "Peptide Nanotubes and Beyond", Chemistry, A European Journal, 4(8): 1367-1372, 1998.
Ghadiri et al. "Self-Assembling Organic Nanotubes Based on A Cyclic Peptide Architecture", Nature, 366: 324-327, 1993.
Horne et al. "A Heterocyclic Peptide Nanotube", Journal of the American Chemical Society, 125(31): 9372-9376, 2003.
Reches et al. "Casting Metal Nanowires Within Discrete Self-Assembled Peptide Nanotubes", Science, 300(5619): 625-627, 2003.
Adekore et al. "Carbon Nanotubes", p. 1-11, 2001.
Brauer "GB-245 Nanotubes: Directions and Techno", BCC, p. 1-14, 2000.
Martin et al. "The Emerging Field of Nanotube Biotechnology", Nature Reviews, 2: 29-37, 2003.
Zhang et al. "Design of Nanostructured Biological Materials Through Self-Assembly of Peptides and Proteins", Current Opinion in Chemical Biology, 6: 865-871, 2002.
Daenen et al. "The Wondrous World of Carbon Nanotubes", p. 1-8, 2003.
Grady et al. "Axe-Txe, A Broad-Spectrum Proteic Toxin-Antitoxin System Specified by a Multidrug-Resistant, Clinical Isolate of *Enterococcus faecium*", Molecular Biology, 47(5): 1419-1432, 2003. Abstract, p. 1424, col. 1—p. 1426, col. 2, Fig.5.
Cherny et al. "The YefM Antitoxin Defines A Family of Natively Unfolded Proteins", The Journal of Biological Chemistry, 279(9): 8252-8261, 2004.
Engelberg-Kulka et al. "Bacterial Programmed Cell Death Systems as Targets for Antibiotics", Trends in Microbiology, 12(2): 66-71, 2004.
Forloni et al. "Anti-Amyloidogenic Activity of Tetracyclines: Studies In Vitro", FEBS Letters, 487(3): 404-407, 2001. Abstract, Results, Figs.1,3.
Lansbury Jr. "Following Nature's Anti-Amyloid Strategy", Nature Biotechnology, 19(2): 112-113, 2001.
Grateau "Le Curli du Coli: Une Variété Physiologique d'Amylose", Medecine Sciences, 18(6-7): 664, 2002.
Cherny et al. "The Formation of *Escherichia coli* Curli Amyloid Fibrils Is Mediated by Prion-Like Peptide Repeats", Journal of Molecular Biology, 352(2): 245-252, 2005.
Gazit "A Possible Role for 'Phi'-Stacking in the Self-Assembly of Amyloid Fibrils", The FASEB Journal, 16: 77-83, 2002.

Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, AN 2003-286683 & RU 2196568 C1 (Kiselev) Jan. 20, 2003. Abstract.
Kon-Ya et al "Indole Derivatives as Potent Inhibitors of Larval Settlement by the Barnacle, Balanus Amphitrite", Bioscience Biotechnology Biochemistry, JP, 58(12): 2178-2181, 1994. Compound 102.
Appukkuttan et al. "Microwave Enhanced Formation of Electron Rich Arylboronates", Synlett, 8: 1204-1206, 2003. Figs. Scheme 4, Compounds 5A, 5B, 5C, 5D.
Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R.: Bulletin de la Société Chimique Française, p. 335-336, 1969.
Soto et al. Beta-Sheet Breaker Peptides Inhibit Fibrillogenesis in A Rat Brain Model of Amyloidosis: Implications for Alzheimer's Therapy, Nature Medicine, 4(7): 822-826, 1998.
Baltzer et al. "De Novo Design of Proteins—What Are the Rules?", Chemical Reviews, 101(10): 3153-3163, 2001. Not to Be IDS'd as per Hadassa (Not Relevant): May 4, 2006.
Inglot "Comparison of the Antiviral Activity In Vitro of Some Non-Steroidal Anti-Inflammatory Drugs", Journal of General Virology, 4(2): 203-214, 1969.
Pavia et al. "Antimicrobial Activity of Nicotine Against A Spectrum of Bacterial and Fungal Pathogens", Journal of Medical Microbiology, 49(7): 675-676, 2000.
Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.
Lee et al. "Anti-Diabetic Constituent From the Node of Lotus Rhizome (Nelumbo Nucifera Gaertn)", Natural Product Sciences, 7(4), 107-109, 2001. p. 108, col. 1, Last §-col. 2, § 1.
Honma et al. "Use of A Thromboxane A2 Antagonist or Synthase Inhibitor for Treating Central Nervous System Diseases, e.g. Alzheimer Type Dementia." Database WPI, Section Ch. Week 200039, Derwent Publications, AN 2000-451668. & WO 00/30683 (Yagami et al.), Jun. 2, 2000. Abstract.
Altland et al. "Potential Treatment of Transthyretin-Type Amyloidoses by Sulfite", Neurogenetics, 2: 183-188, 1999.
Azriel et al. "Analysis of the Minimal Amyloid-Forming Fragment of the Islet Amyloid Polypeptide", The Journal of Biological Chemistry, 276(36): 34156-34161, 2001.
Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.
Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.
Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.
Kocisko et al. "New Inhibitors of Scrabie-Associated Prion Protein Formation in A Library of 2,000 Drugs and Natural Products", Journal of Virology, 77(19): 10288-10294, 2003.
Lashuel et al. "New Class of Inhibitors of Amyloid-β Fibril Formation. Implications for the Mechanism of Pathogenesis in Alzheimer's Disease", The Journal of Biological Chemistry, 277(45): 42881-42890, 2002.
Oza et al. "Synthesis and Evaluation of Anthranilic Acid-Based Transthyretin Amyloid Fibril Inhibitors", Bioorganic & Medicinal Chemistry Letters, 9: 1-6, 1999.

Peterson et al. "Inhibiting Transthyretin Conformational Changes That Lead to Amyloid Fibril Formation", Proc. Natl. Acad. Sci. USA, 95: 12956-12960, 1998.

Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.

Lazaris et al. "Spider Silk Fibers Spun From Soluble Recombinant Silk Produced in Mammalian Cells", Science, 295: 472-476, 2002. p. 474-475.

Gazit "Mechanisms of Amyloid Fibril Self-Assembly and Inhibition Model Short Peptides as A Key Research Tool", The FEBS Journal, 272: 5971-5978, 2005.

Jack et al. "The Organization of Aromatic Side Groups in An Amyloid Fibril Probed by Solid-State 2H and 19F NMR Spectroscopy", Journal of the American Chemical Society, JACS, 128: 8098-8099, 2006.

Reches et al. "Designed Aromatic Homo-Dipeptides: Formation of Ordered Nanostructures and Potential Nanotechnological Applications", Physical Biology, 3: S10-S19, 2006.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1):68-76, 2000.

Anguiano et al. "Protofibrillar Islet Amyloid Polypeptide Permeabilizes Synthetic Vesicles by A Pore-Like Mechanism That May Be Relevant to Type II Diabetes", Biochemistry, 41: 11338-11343, 2002.

Arvinte et al. "The Structure and Mechanism of Formation of Human Calcitonin Fibrils", The Journal of Biological Chemistry, 268(9): 6415-6422, 1993.

Austin et al. "Medical Progress: Calcitonin. Physiology and Pathophysiology", The New England Journal of Medicine, 304(5): 269-278, 1981.

Balaram "De Novo Design: Backbone Conformational Constraints in Nucleating Helices and β-Hairpins", Journal of Peptide Research, 54: 195-199, 1999.

Balbach et al. "Supramolecular Structure in Full-Length Alzheimer's β-Amyloid Fibrils: Evidence for A Parallel β-Sheet Organization From Solid-State Nuclear Magnetic Resonance", Biophysical Journal, 83: 1205-1216, 2002.

Bauer et al. "Interfacial Adsorption and Aggregation Associated Changes in Secondary Structure of Human Calcitonin Monitored by ATR-FTIR Spectroscopy", Biochemistry, 33: 12276-12282, 1994.

Benvenga et al. "Homology of Calcitonin With the Amyloid-Related Proteins", Journal of Endocrinological Investigation, 17: 119-122, 1994.

Berger et al. "Calcitonin-Like Immunoreactivity of Amyloid Fibrils in Medullary Thyroid Carcinomas", Virchows Archiv A Pathological Anatomy and Histopathology, 412: 543-551, 1988.

Berson et al. "Proprotein Convertase Cleavage Liberates A Fibrillogenic Fragment of A Resident Glycoprotein to Inititate Melanosome Biogenesis", Journal of Cell Biology, 161(3): 521-533, 2003.

Bird et al. "Single-Chain Antigen-Binding Proteins", Science, 242(4877): 423-426, 1988.

Boerner et al. "Production of Antigen-Specific Human Monoclonal Antibodies From In Vitro-Primed Human Splenocytes", The Journal of Immunology, 147(1): 86-95, 1991.

Bong et al. "Self-Assembling Organic Nanotubes", Angewandte Chemie, International Edition,40:988-1011, 2001.

Chapman et al. "Role of *Escherichia coli* Curli Operons in Directing Amyloid Fiber Formation", Science, 295(5556): 851-855, 2002, Abstract.

Cherny et al. "The Formation of Curli Amyloid Fibrils Is Mediated by Prion-Like Peptide Repeats", Biophysical Journal, 86(1): 508A & 48th Annual Meeting of the Biophysical Society, Baltimore, MD, USA, 2004.

Cherny et al. "The Formation of *Escherichia Coli* Curli Amyloid Fibrils in Mediated by Prion-Like Peptide Repeats", Journal of Molecular Biology, 352(2): 245-252, 2005.

Cherny et al. "The YefM Antitoxin Defines a Family of Natively Unfolded Proteins", J. Biol. Chem., vol. 279 (9), p. 8252-8261, 2004.

Choplin "Computers and the Medicinal Chemist", Comprehensive Medicinal Chemistry, 4(Chap.17.2): 33-58, 1990.

Chou et al. "Conformational Parameters for Amino Acids in Helical, β-Sheet, and Random Coil Regions Calculated From Proteins", Biochemistry, 13(2): 211-222, 1974.

Chou et al. "Empirical Predictions of Protein Conformation", Annual Reviews in Biochemistry, 47: 251-276, 1978.

Claessen et al. "A Novel Class of Secreted Hydrophodic Proteins is Involved in Aerial Hyphae Formation in Streptomyces Coelicolor by Forming Amyloid-Like Fibrils", Genes & Development, 17: 1714-1726, 2003.

Claessens et al. "Review Commentary: π-π Interactions in Self-Assembly", Journal of Physical Organic Chemistry, 10: 254-272, 1997.

Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.

Copp "Endocrine Regulation of Calcium Metabolism", Annual Reviews in Physiology, 32: 61-86, 1970.

Elliot et al. "The Chaplins: A Family of Hydrophobic Cell-Surface Proteins Involved in Aerial Mycelium Formation in Streptomyces Coelicolor", Genes & Development, 17: 1727-1740, 2003.

Engelberg-Kulka et al. "Bacterial Programmed Cell Death Systems as Targets for Antibodies", Trends in Microbiology, vol. 12 (2): p. 66-71, 2004.

Findeis et al. "Modified-Peptide Inhibitors of Amyloid β-Peptide Polymerization", Biochemistry, 38: 6791-6800, 1999.

Fingl et al. "Introduction: General Principles", The Pharmacological Basis of Therapeutics, 5th Ed., Sec. 1(Chap.1): 1-53, 1975.

Fishwild et al., "High-Avidity Hum IgGk Monoclonal Antibodies From A Novel Strain of Minilocus Transgenic Mice", Nature Biotechnology, 14: 845-851, 1996.

Forloni et al. "Anti-Amyloidogenic Activity of Tetracyclines: Studies in Vitro", FEBS Letters, 487(3): 404-407, 2001. Figs. 1,3.

Gazit "Mechanisms of Amyloid Fibril Self-Assembly and Inhibition Model Short Peptides as A Key Research Tool", The FEBS Journal, 272: 5971-5978, 2005.

Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.

Ghadiri et al. "Artificial Transmembrane Ion Channels From Self-Assembling Peptide Nanotubes", Nature, 369(6478): 301-304, 1994.

Gillard et al. "Controlling Self-Assembly", Chemical European Journal, 3(12): 1933-1940, 1997.

Görbitz "Nanotube Formation by Hydrophobic Dipeptides", Chemistry, 7(23): 5153-5159, 201, Abstract.

Grady et al. "Axe-Txe, A Broad-Spectrum Proteic Toxin-Antitoxin System Specified by a Multi-Resistant, Clinical Isolate of Enterococcus Faecium", Molecular Microbiology, vol. 47(5: p. 1419-1432, 2003.

Grateau "[Coli's Curli or How Amyloid Can be Physiological.]", Médecine Sciences, 18(6-7): p. 664, 2002.

Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.

Halder et al. "First Crystallographic Signature of the Highly Ordered Supramolecular Helical Assemblage from a Tripeptide Containing a Non-Coded Amino Acid", Terahedron Letters, 43(14): 2653-2656, 2002, Abstract.

Harlow et al. "Antibodies: A Laboratory Manual", Cold Spring Harbor Laboratory, p. III-IX, 1988.

Harrison et al. "Amyloid Peptides and Proteins in Review", Reviews in Physiology, Biochemistry and Pharmacology, 159: 1-77, 2007.

Hartgerink et al. "Peptide Nanotubes and Beyond", Chemistry European Journal, 4(8): 1367-1372, 1998, Abstract.

Holmes et al. "Extensive Neurite Outgrowth and Active Synapse Formation on Self-Assembling Peptide Scaffolds", Proc. Natl. Acad. Sci. USA, 97(12): 6728-6733.

Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.

Horne et al. JACS, 125: 9372-9376, 2003.

Hoyle et al. "Pseudomonas Aeruginosa Biofilm as A Diffusion Barrier to Piperacillin", Antimicrobial Agents and Chemotherapy, 36(9): 2054-2056, 1992.

Huang et al. "A Review on Polymer Nanofibers by Electrospinning and Their Applications in Nanocomposites", Composites Science and Technology, 63: 2223-2253, 2003.

Inbar et al. "Localization of Antibody-Combining Sites Within the Variable Portions of Heavy and Light Chains", Proc. Natl. Acad. Sci. USA, 69(9): 2659-2662, 1972.

Jack et al. "The Organization of Aromatic Side Groups in An Amyloid Fibril Probed by Solid-State 2H and 19F NMR Spectroscopy", Journal of the American Chemical Society, JACS, 128: 8098-8099, 2006.

Jayawarna et al. "Nanostructured Hydrogels for Three-Dimensional Cell Culture Through Self-Assembly of Fluorenylmethoxycarbonyl-Dipeptides", Advanced Materials, 18: 611-614, 2006.

Jin "Electrospinning Bombyx Mori Silk With Poly (Ethylene Oxide)" Biomacromolecules, 3: 1233-1239, 2002.

Jones et al. "Replacing the Complementarity-Determining Regions in A Human Antibody With Those From A Mouse", Nature, 321: 522-525, 1986.

Kamihira et al. "Conformational Transitions and Fibrillation Mechanism of Human Calcitonin as Studied by High-Resolution Solid-State 13C NMR [in Process Citation]", Protein Science, 9: 867-877, 2000.

Kanaori et al. "Study of human Calcitonin Fibrillation by Proton Nuclear Magnetic Resonance Spectroscopy", Biochemistry, 34: 12138-12143, 1995.

Kaplan "Fibrous Proteins-Silk as A Model System", Polymer Degradation and Stability, 59: 25-32, 1998.

Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.

Kedar et al. "In Vitro Synthesis of 'Amyloid' Fibrils From Insulin, Calcitonin and Parathormone", Israel Journal of Medical Science, 12(10): 1137-1140, 1976.

Kubik "High-Performance Fibers From Spider Silk", Angewandte Chemie, International Edition, 41(15): 2721-2723, 2002.

Kyte et al. "A Simple Method for Displaying the Hydropathic Character of A Protein", Journal of Molecular Biology, 157: 105-132, 1982.

Lansbury "Following Nature's Anti-Amyloid Strategy", Nature Biotechnology, 19(2): 112-113, 2001. p. 112, Left-Hand Col., Paragraph 1 - Middle Col., Paragraph 1.

Larrick et al. "PCR Amplification of Antibody Genes", Methods: A Companion to Methods in Enzymology, 2(2): 106-110, 1991.

Lazaris et al. "Spider Silk Fibers Spun From Soluble Recombinant Silk Produced in Mammalian Cells", Science, 295: 472-476, 2002, p. 474-475.

Lee et al. "Virus-Based Febrication of Micro- and Nanofibers Using Electrospinnig" Nano Letters, 4(3): 387-390, 2004.

Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.

Lonberg et al. "Antigen-Specific Human Antibodies From Mice Comprising Four Distinct Genetic Modifications", Nature, 368(6474): 856-859, 1994.

Lonberg et al. "Human Antibodies From Transgenic Mice", International Review of Immunology, 13: 65-93, 1995.

Lowe et al. "Structure-Function Relationships for Inhibitors of β-Amyloid Toxicity Containing the Recognition Sequence KLVFF", Biochemistry, 40: 7882-7889, 2001.

Lyon et al. "Self-Assembly and Gelation of Oxidized Gluthathione in Organic Solvents", Journal of the American Chemical Society, 123: 4408-4413, 2001.

Mah et al. "A Genetic Basis for Pseudomonas Aeruginosa Biofilm Antibiotic Resistance", Nature, 426: 306-310, 2003.

Maji et al. "Fibril-Forming Model Synthetic Peptides Containing 3-Aminophenylacetic Acid", Tetrahedron, 58(43): 8695-8702, 2002, Abstract.

Marks et al. "By-Passing Immunization - Human Antibodies from V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Matsui et al. "Crystalline Glyclylglycine Bolaamphiphile Tubules and Their pH-Sensitive Structural Transformation" The Journal of Physical Chemistry B, 104(15): 3384-3386, 2000.

Maury et al. "Creation of Amyloid Fibrils From Mutant ASN187 Gelsolin Peptides", Biochemical and Biophysical Research Communications, 183(1): 227-231, 1992.

McGaughey et al. "π-Stacking Interactions", The Journal of Biological Chemistry, 273(25): 15458-15463, 1998.

Meluleni et al. "Mucoid Pseudomonas Aeruginose Growing in A Biofilm in Vitro are Killed by Opsonic Antobodies to the mucoid Exopolysaccharide Capsule but Not by Antibodies Produced During Chronic Lung Infection in Cystic Fibrosis Patients,", Journal of Immunology, 155:2029-2038, 1995.

Morrison "Success in Specification", Nature, 368(6474): 812-813, 1994.

Mosmann "Rapid Colorimetric Assay for Cellular Growth and Survival: Application to Proliferation and Cytotoxicity Assays", Journal of Immunological Methods, 65: 55-63, 1983.

Mosselman et al. "The Complete Islet Amyloid Polypeptide Precursor Is Encoded by Two Exons", FEBS Letters, 247: 154-158, 1989, Database Accession No. S04016.

Murphy et al. "Biofilm Formation by Nontypeable Haemophilus Influenzae: Strain variability, Outer Membrane Antigen Expression and Role of pili", BMC Microbiology, 2(7): 1471-2810, 2002.

Mutter "Studies on the Coupling Rates in Liquid-Phase Peptide Synthesis Using Competition Experiments", International Journal of Peptide Protein Research, 13: 274-277, 1979.

Neuberger "Generating High-Avidity Human Mabs in Mice", Nature Biotechnology, 14: 826, 1996.

Nicolaus "Symbiotic Approach to Drug Design", Decision Making in Drug Research, p. 173-186, 1983.

Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.

Pack et al. "Improved Bivalent Miniantibodies, With Identical Avidity as Whole Antibodies, Produced by High Cell Density Fermentation of *Escherichia Coli*", Bio-Technology, 11: 1271-1277, 1993.

Petkova et al. "A Structural Model for Alzheimer's β-Amyloid Fibrils Based on Experimental Constraints From Solid State NMR", Proc. Natl. Acad. Sci. USA, 99(26): 16742-16747, 2002.

Pettmann et al. "Morphological and Biochemical Maturation of Neurones Cultured in the Absence of Glial Cells", Nature, 281: 378-380, 1979.

Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.

Porter "The Hydrolysis of Rabbit γ-Globulin and Antibodies With Crystalline Papain", Biochemical Journal, 73: 119-126, 1959.

Presta "Antibody Engineering", Current Opinion in Structural Biology, 2: 593-596, 1992.

Puchtler et al. "A Review of Early Concepts of Amyloid in Context With Contemporary Chemical Literature From 1839 to 1859", The Journal of Histochemistry and Cytochemistry, 14(2): 123-134, 1966.

Reches et al. "Amyloid Fibril Formation by Pentapeptide and Tetrapeptide Fragments of Human Calcitonin", The Journal of Biological Chemistry, 277(38): 35475-35480, 2002.

Reches et al. "Casting Metal Nanowires Within Discrete Self-Assembled Peptide Nanotubes", Science, 300(5619): 625-627, 2003, Abstract.

Reches et al. "Designed Aromatic Homo-Dipeptides: Formation of Ordered Nanostructures and Potential Nanotechnological Applications", Physical Biology, 3: S10-S19, 2006.

Reches et al. "Self-Assembly of Peptide Nanotubes and Amylois-Like Structures by Charged-Termini-Capped Diphenylalanine Peptide Analogues", Israel Journal of Chemistry, 45(3): 363-371, 2005.

Reches et al. "Supporting Online Material", Science, 300(5619): 1-9, 2003. Retrieved From the Internet: URL:http://www.sciencemag.org/cgi/data/300/5619/625/DCI.

Reza et al. Nature, 366: 324-327, 1993.

Riechmann et al. "Reshaping Human Antibodies for Therapy", Nature, 332: 323-329, 1988.

Sacchettini et al. "Therapeutic Strategies for Human Amyloid Diseases", Nature Reviews: Drug Discovery, 1: 267-275, 2002.

Shetty et al. "Aromatic π-Stacking in Solution as Revealed Through the Aggregation of Phenylacetylene Macrocycles", Journal of the American Chemical Society, 118: 1019-1027, 1996.

Sigel-Causey et al. "Phylogeny of the Pelecaniformes: Molecular Systematics of A Privative Group", Avian Molecular Evolution and Systematics, academic Press, p. 159-171, NBCI GenBank, Accession No. AAB58518, 1997.

Solomon et al. "Disaggregation of Alzheimer β-Amyloid by Site-Directed MAb", Proc. Natl. Acad. Sci. USA, 94: 4109-4112, 1997.

Stewart "Theoretical Aspects of Antibiotic Diffusion Into Microbial Biofilms", Antimicrobial Agents and Chemotherapy, 40(11): 2517-2522, 1996.

Sun et al. "Aromatic Van der Waals Clusters: Structure and Nonrigidity", Journal of Physical Chemistry, 100: 13348-13366, 1996.

Tjernberg et al. "Arrest of β-Amyloid Fibril Formation by A Pentapeptide Ligand", The Journal of Biological Chemistry, 271(15): 8545-8548, 1996.

Tjernberg et al. "Controlling Amyloid β-Peptide Fibril Formation With Protease-Stable Ligands", The Journal of Biological Chemistry, 272(19): 12601-12605, 1997.

Toledano et al. "Enzyme-Triggered Self-Assembly of Peptide Hydrogels Via Reversed Hydrolysis", Journal of the American Chemical Society, JACS, 128(4): 1070-1071, 2006.

Tonkinson et al. "Antisense Oligodeoxynucleotides as Clinical Therapeutic Agents", Cancer Investigation, 14(1): 54-65, 1996.

True et al. "Epigenetic Regulation of Trenslation Reveals Hidden Genetic Variation to Produce Complex Traits", Nature, 431: 184-187, 2004.

Tsai et al. "Synthesis of AIB-Containing Peptidomimetics as Potential Inhibitors of Alzheimer's π-Secretase", 218th ACS National Meeting, New Orleans, USA, Meeting Abstract, MEDI-018, 1999. Abstract.

Tsang et al. "A Simple Chemical Method of Opening and Filling Carbon Nanotubes", Nature, 372: 159-162, 1994.

Tuite et al. "Propagation of Yeast Prions", Nature Reviews, 4: 878-889, 2003.

Vauthey et al. "Molecular Self-assembly of Surfactant-Like Peptides to form Nanotubes and Nanovesicles", PNAS, 99(8):5355-5360, 2002.

Verhoeyen et al. "Reshaping Human Antibodies: Grafting An Antilsozyme Activity", Science, 239: 1534-1536, 1988.

Vidal et al. "A Stop-Codon Mutation int he BRI Gene Associated With Familial British Dementia", Nature, 399: 776-781, 1999.

Whitlow et al. "Single-Chain Fv Proteins and Their Fusion Proteins", Methods: A Companion to Methods in Enzymology, 2(2): 97-105, 1991.

Wolfenden et al. "Affinities of Amino Acid Side Chains for Solvent Water", Biochemistry, 20: 849-855, 1981.

Yokoi et al. "Dynamic Reassembly of Peptide RADA16 Nanofiber Scaffold", Proc. Natl. Acad. Sci. USA, 102(24): 8414-8419, 2005.

Zaidi et al. "Forty Years of Calcitonin - Where Are We Now? A Tribute to the Work of Iain Macintyre, FRS", Bone, 30(5): 655-663, 2002.

Zhang et al. "Supramolecular Hydrogels Respond to Ligand-Receptor Interaction", Journal of the American Chemical Society, 125(45): 13680-13681, 2003.

* cited by examiner

```
                           SEQUENCE LISTING

<160> NUMBER OF SEQ ID NOS: 13

<210> SEQ ID NO 1
<211> LENGTH: 2
<212> TYPE: PRT
<213> ORGANISM: Artificial sequence
<220> FEATURE:
<223> OTHER INFORMATION: Synthetic peptide

<400> SEQUENCE: 1

Phe Phe
1

<210> SEQ ID NO 2
<211> LENGTH: 2
<212> TYPE: PRT
<213> ORGANISM: Artificial sequence
<220> FEATURE:
<223> OTHER INFORMATION: Synthetic peptide

<400> SEQUENCE: 2

Trp Trp
1

<210> SEQ ID NO 3
<211> LENGTH: 2
<212> TYPE: PRT
<213> ORGANISM: Artificial sequence
<220> FEATURE:
<223> OTHER INFORMATION: Synthetic peptide

<400> SEQUENCE: 3

Trp Tyr
1

<210> SEQ ID NO 4
<211> LENGTH: 2
<212> TYPE: PRT
<213> ORGANISM: Artificial sequence
<220> FEATURE:
<223> OTHER INFORMATION: Synthetic peptide

<400> SEQUENCE: 4

Trp Phe
1

<210> SEQ ID NO 5
<211> LENGTH: 2
<212> TYPE: PRT
<213> ORGANISM: Artificial sequence
<220> FEATURE:
<223> OTHER INFORMATION: Synthetic peptide

<400> SEQUENCE: 5

Phe Trp
1

<210> SEQ ID NO 6
<211> LENGTH: 2
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Phenylglycine

<400> SEQUENCE: 6

Xaa Xaa
1

<210> SEQ ID NO 7
<211> LENGTH: 3
<212> TYPE: PRT
<213> ORGANISM: Artificial sequence
<220> FEATURE:
<223> OTHER INFORMATION: Synthetic peptide

<400> SEQUENCE: 7

Cys Phe Phe
1

<210> SEQ ID NO 8
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D stereoisomer

<400> SEQUENCE: 8

Phe Phe
1

<210> SEQ ID NO 9
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: naphthylalanine

<400> SEQUENCE: 9

Xaa Xaa
1

<210> SEQ ID NO 10
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: pentafluro-phenylalanine

<400> SEQUENCE: 10

Xaa Xaa
1
```

```
<210> SEQ ID NO 11
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: iodo-phenylalanine

<400> SEQUENCE: 11

Xaa Xaa
1

<210> SEQ ID NO 12
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: 4-phenyl phenylalanine

<400> SEQUENCE: 12

Xaa Xaa
1

<210> SEQ ID NO 13
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: p-nitro-phenylalanine

<400> SEQUENCE: 13

Xaa Xaa
1
```

PEPTIDE NANOSTRUCTURES ENCAPSULATING A FOREIGN MATERIAL AND METHOD OF MANUFACTURING SAME

This is a continuation in part of PCT/IL2004/000012, filed Jan. 7, 2004, which claims priority of U.S. Provisional Patent Application Nos. 60/438,331, filed Jan. 7, 2003 and 60/458,378, filed Mar. 31, 2003

FIELD AND BACKGROUND OF THE INVENTION

The present invention relates to peptide nanostructures and more specifically to peptide nanostructures encapsulating foreign materials.

Nanoscience is the science of small particles of materials and is one of the most important research frontiers in modern technology. These small particles are of interest from a fundamental point of view since they enable construction of materials and structures of well-defined properties. With the ability to precisely control material properties come new, opportunities for technological and commercial development, and applications of nanoparticles have been shown or proposed in areas as diverse as micro- and nanoelectronics, nanofluidics, coatings and paints and biotechnology.

It is well established that future development of microelectronics, magnetic recording devices and chemical sensors will be achieved by increasing the packing density of device components. Traditionally, microscopic devices have been formed from larger objects, but as these products get smaller, below the micron level, this process becomes increasingly difficult. It is therefore appreciated that the opposite approach is to be employed, essentially, the building of microscopic devices from a molecular level up, primarily via objects of nanometric dimensions. Self-assembled nanoparticles, such as nanotubes and nanospheres, allow controlled fabrication of novel nanoscopic materials and devices. Such nanostrcutures have found use in areas as diverse as micro- and nanoelectronics, nanofluidics, coatings and paints and biotechnology.

In particular, wire-like semiconducting nanostructures have attracted extensive interest over the past decade due to their great potential for addressing some basic issues about dimensionality and space confined transport phenomena as well as related applications. Wire-like semiconducting nanostructures often have distinctive properties and can be used as transparent conducting materials and gas sensors. For example, fluorine-doped tin oxide films are used in architectural glass applications because of their low emissivity for thermal infrared heat. Tin-doped indium oxide films can be used for flat panel displays due to their high electrical conductivity and high optical transparency.

In the field of magnetic recording, wire-like nanostructures can be used as magnetoresistive read transducers. It has been well known that the magnetoresistive sensors are capable of reading information from the surface of magnetic recording media at high linear densities. The magnetoresistive sensors sense magnetic signals by way of the electrical resistance change of magnetoresistive elements that varies as a function of the strength and orientation of the magnetic flux sensed by read or magnetoresistive elements. The use of nanoscale elements in such sensors significantly increases the capability of retrieving accurate information from highly dense magnetic media.

In the field of displays, much effort has been devoted to developed electrophoretic displays. Such displays use a display medium comprising a plurality of electrically charged particles suspended in a fluid. Electrodes are provided adjacent the display medium so that the charged particles can be moved through the fluid by applying an electric field to the medium. In one type of such electrophoretic display, the medium comprises a single type of particle having one optical characteristic in a fluid which has a different optical characteristic. In a second type of such electrophoretic display, the medium contains two different types of particles differing in at least one optical characteristic and in electrophoretic mobility.

The most widely used building blocks of nano-materials and nano-devices are the fullerene carbon nanotubes. Two major forms of carbon nanotubes exist, single-walled nanotubes (SWNT), which can be considered as long wrapped graphene sheets and multi walled nanotubes (MWNT) which can be considered as a collection of concentric SWNTs with different diameters.

SWNTs have a typical length to diameter ratio of about 1000 and as such are typically considered nearly one-dimensional. These nanotubes consist of two separate regions with different physical and chemical properties. A first such region is the side wall of the tube and a second region is the end cap of the tube. The end cap structure is similar to a derived from smaller fullerene, such as $C_{60}$.

Since nanotubes have relatively straight and narrow channels in their cores, it was initially suggested that these cavities may be filled with foreign materials to fabricate one dimensional nanowires. Early calculations suggested that strong capillary forces exist in nanotubes, which are sufficient to hold gases and fluids inside them [Pederson (1992) Phys. Rev. Lett. 69:2689]. The first experimental proof was provided by Pederson and co-workers, who showed filling and solidification of molten leaf inside nanotubes [Pederson (1992) Phys. Rev. Lett. 69:415]. Various other examples, concerning the filling of nanotubes with metallic and ceramic materials exist in the literature [Ajayan (1993) Nature 361:392; Tsang (1994) Nature 372:416; Dujardin (1994) 265:1850].

Despite high applicability, the process of filling carbon nanotubes is difficult and inefficient. Most commonly produced carbon nanotubes, are capped at at least one end of the tube and no method for efficiently opening and filling the carbon nanotubes with foreign material is known to date. For example, nanotube ends can be opened by post oxidation treatment in an oxygen atmosphere at high temperature. The major drawback of such a procedure is that the tube ends become filled with carbonaceous debris. As a consequent, filling the open-ended tubes after post oxidation with other material has proven difficult. Another problem with carbon nanotubes synthesized in inert gas arcs is the formation of highly defective tubes containing amorphous carbon deposits on both the inside surface and outside surface of the tubes and the presence of discontinuous graphite sheets. Furthermore, since carbon nanotubes are curved, wetting may prove difficult. Finally, since the internal cavity of SWNTs is very small, filling can be done only for a very limited number of materials.

Recently, peptide building blocks have been shown to form nanotubes. Peptide nanotubes are of a special interest since they are biocompatible and can be easily chemically modified.

Peptide-based nanotubular structures have been made through stacking of cyclic D-, L-peptide subunits. These peptides self-assemble through hydrogen-bonding interactions into nanotubules, which in-turn self-assemble into ordered parallel arrays of nanotubes [Ghadiri, M. R. et al., Nature 366, 324-327 (1993); Ghadiri, M. R. et al., Nature 369, 301-304 (1994); Bong, D. T. et al., Angew. Chem. Int. Ed. 40, 988-1011 (2001)].

More recently, surfactant-like peptides that undergo spontaneous assembly to form nanotubes with a helical twist have been reported. The monomers of these surfactant peptides have distinctive polar and nonpolar portions. They are composed of 7-8 residues, approximately 2 nm in length when fully extended, and dimensionally similar to phospholipids found in cell membranes. Although the sequences of these peptides are diverse, they share a common chemical property, i.e., a hydrophobic tail and a hydrophilic head. These peptide nanotubes, like carbon and lipid nanotubes, also have a very high surface area to weight ratio. Molecular modeling of the peptide nanotubes suggests a possible structural organization [Vauthey (2002) Proc. Natl. Acad. Sci. USA 99:5355; Zhang (2002) Curr. Opin. Chem. Biol. 6:865]. Based on observation and calculation, it is proposed that the cylindrical subunits are formed from surfactant peptides that self-assemble into bilayers, where hydrophilic head groups remain exposed to the aqueous medium. Finally, the tubular arrays undergo self-assembly through non-covalent interactions that are widely found in surfactant and micelle structures and formation processes.

Peptide based bis(N-α-amido-glycyglycine)-1,7-heptane dicarboxylate molecules were also shown to be assembled into tubular structures [Matsui (2000) J. Phys. Chem. B 104: 3383].

However, although at least some of the above-described peptides were shown to form open-ended nanotubes [Hartgerink (1996) J. Am. Cham. Soc. 118:43-50], these are composed of peptide building blocks, which are relatively long and as such are expensive and difficult to produce, or limited by heterogeneity of structures that are formed as bundles or networks rather than discrete nanoscale structures.

There is thus a widely recognized need for, and it would be highly advantageous to have, hollow peptide nanostructures, which are devoid of the above limitations.

SUMMARY OF THE INVENTION

According to one aspect of the present invention there is provided a composition comprising a material at least partially enclosed by a tubular, spherical or planar nanostructure composed of a plurality of peptides, wherein each of the plurality of peptides includes no more than 4 amino acids and whereas at least one of the 4 amino acids is an aromatic amino acid.

According to another aspect of the present invention there is provided a method of encapsulating material in a tubular, spherical or planar nanostructure, the method comprising: (a) providing the tubular or spherical nanostructure composed of a plurality of peptides, wherein each of the plurality of peptides includes no more than 4 amino acids and whereas at least one of the 4 amino acids is an aromatic amino acid, the tubular or spherical nanostructure having an internal cavity; and (b) introducing the material into the internal cavity of the tubular or spherical nanostructure, thereby encapsulating the material in the tubular or spherical nanostructure.

According to yet another aspect of the present invention there is provided a method of encapsulating material in a tubular, spherical or planar nanostructure, the method comprising assembling the tubular or spherical nanostructure composed of a plurality of peptides, wherein each of the plurality of peptides includes no more than 4 amino acids and whereas at least one of the 4 amino acids is an aromatic amino acid in the presence of the material, thereby encapsulating the material on the tubular or spherical nanostructure.

According to still another aspect of the present invention there is provided a composition comprising a material at least partially enclosed by a tubular, spherical or planar nanostructure composed of polyaromatic peptides.

According to an additional aspect of the present invention there is provided a method of positioning a target molecule at a predetermined location, the method comprising: (a) providing a magnetic nanowire having at least one segment associated with a functional group or ligand, the functional group or ligand being capable of binding to the target molecule; (b) binding the magnetic nanowire to the target molecule; and (c) exposing the magnetic nanowire to a magnetic field, so as to position the magnetic nanowire and the target molecule at the predetermined location; wherein the nanowire is formed of a magnetic material at least partially enclosed by a nanostructure composed of a plurality of peptides, each of the plurality of peptides including no more than 4 amino acids, whereas at least one of the 4 amino acids is an aromatic amino acid.

According to further features in preferred embodiments of the invention described below, the functional group, is selected from the group consisting of thiols, disulfides, cyanides, amines, carboxylic acids, phosphonates, siloxanes and hydroxamic acids.

According to still further features in the described preferred embodiments the ligand is selected from the group consisting of proteins, fibronectin, DNA, RNA, enzymes, ribozymes, hydrophobic materials, hydrophillic materials, cells, tissue, microorgantisms, bacteria, viruses and chemoattractant.

According to still further features in the described preferred embodiments the method further comprises monitoring the target molecule using a light-emitting material at least partially enclosed by the nanostructure.

According to yet an additional aspect of the present invention there is provided a method of delivering an agent to a subject, the method comprising: providing a composition having the agent at least partially enclosed by a tubular, spherical or planar nanostructure; and administrating the nanostructure to the subject; wherein the nanostructure is composed of a plurality of peptides, each of the plurality of peptides including no more than 4 amino acids and whereas at least one of the 4 amino acids is an aromatic amino acid.

According to still further features in the described preferred embodiments the agent is a therapeutic agent.

According to still further features in the described preferred embodiments the therapeutic agent is an anti-cancer drug.

According to still further features in the described preferred embodiments, the method further comprises monitoring the agent using a light-emitting material at least partially enclosed by the nanostructure.

According to still an additional aspect of the present invention there is provided a thermoelectric device, comprising a first heat conducting layer and a second heat conducting layer, the first and the second heat conducting layers being interposed by a plurality of nanowires, such that when current flows through the plurality of nanowires, heat is transferred out of the first heat conducting layer and is dissipated through the second heat conducting layer wherein each of the plurality of nanowires is formed of a thermoelectric material at least partially enclosed by a nanostructure composed of a plurality of peptides, and wherein each of the plurality of peptides includes no more than 4 amino acids, such that at least one of the 4 amino acids is an aromatic amino acid.

According to a further aspect of the present invention there is provided a thermoelectric system having an arrangement of thermoelectric devices, each one of the thermoelectric devices comprising a first heat conducting layer and a second heat conducting layer, the first and the second heat conducting layers being interposed by a plurality of nanowires, such that when current flows through the plurality of nanowires, heat is transferred out of the first heat conducting layer and is dissipated through the second heat conducting layer; wherein each of the plurality of nanowires is formed of a thermoelectric material at least partially enclosed by a nanostructure composed of a plurality of peptides, and wherein each of the plurality of peptides includes no more than 4 amino acids, such that at least one of the 4 amino acids is an aromatic amino acid.

According to yet a further aspect of the present invention there is provided a thermoelectric device, comprising at least three heat conducting regions and at least one semiconducting region being connected to at least one heat conducting region of the at least three heat conducting regions via at least one nanowire formed of a conducting or thermoelectric material, at least partially enclosed by a nanostructure composed of a plurality of peptides, each of the plurality of peptides including no more than 4 amino acids, whereas at least one of the 4 amino acids is an aromatic amino acid; the at least three heat conducting regions and the at least one semiconducting region being arranged, in the thermoelectric device such that when current flows therethrough, heat is transferred out of at least one of the at least three heat conducting regions.

According to further features in, preferred embodiments of the invention described below, the at least one semiconducting region is formed of a material selected from the group consisting of CdS, CdSe, ZnS and $SiO_2$.

According to still a further aspect of the present invention there is provided a method of characterizing a nucleic acid sequence of a polynucleotide, the method comprising: (a) positioning the polynucleotide in a nanogate defined by two conducting nanowires, each of the two conducting nanowires being formed of a conducting material at least partially enclosed by a nanostructure composed of a plurality of peptides, each of the plurality of peptides including no more than 4 amino acids, wherein at least one of the 4 amino acids is an aromatic amino acid; (b) applying a tunneling voltage to the nanogate so as to generate electron tunneling between the two conducting nanowires; and (c) measuring at least one parameter characteristic of the nucleic acid sequence of the polynucleotide.

According to further features in preferred embodiments of the invention described below, the positioning the molecule is by generating an electric field capable of inducing electrophoresis forces on the polynucleotide.

According to still a further aspect of the present invention there is provided an apparatus for characterizing a nucleic acid sequence of a polynucleotide, the apparatus comprising: (a) a nanogate defined by two conducting nanowires, each of the two conducting nanowires being formed of a conducting material at least partially enclosed by a nanostructure composed of a plurality of peptides, each of the plurality of peptides including no more than 4 amino acids, wherein at least one of the 4 amino acids is an aromatic amino acid; and (b) a positioning device for positioning the polynucleotide within the nanogate; the positioning device and the nanogate being is designed and constructed such that when the polynucleotide is positioned within the nanogate and a voltage is applied thereto, electron tunneling is generated between the two conducting nanowires, the electron tunneling having at least one parameter characteristic of the nucleic acid sequence of the polynucleotide.

According to further features in preferred embodiments of the invention described below, the positioning the molecule comprises an arrangement of electrodes designed and constructed to generate an electric field capable of inducing electrophoresis forces on the polynucleotide.

According to still further features in the described preferred embodiments the at least one parameter is selected from the group consisting of a tunneling current, a tunneling current-voltage curve, a tunneling current derivative, a current-slope-voltage curve and a dielectric constant.

According to still a further aspect of the present invention there is provided a display system comprising: (a) a fluid containing a plurality of nanostructure devices each being formed of a conducting or semiconducting material at least partially enclosed by a nanostructure composed of a plurality of peptides, each of the plurality of peptides including no more than 4 amino-acids, whereas at least one of the 4 amino acids is an aromatic amino acid; (b) an electric field generator capable of generating an electric field effective in shifting the nanostructure devices between a dispersed state and an aggregated state; wherein a size of the nanostructure devices is selected such that when the nanostructure devices are in the dispersed state, the fluid presents a first optical characteristic, and when the nanostructure devices are in the aggregated state, the fluid presents a second optical characteristic.

According to further features in preferred embodiments of the invention described below, the first and the second optical characteristics comprise characteristic wavelength.

According to still further features in the described preferred embodiments the first and the second optical characteristics comprise characteristic intensity.

According to still further features in the described preferred embodiments the first and the second optical characteristics comprise characteristic wavelength and characteristic intensity.

According to still further features in the described preferred embodiments the nanostructure devices comprises a light-emitting material.

According to still a further aspect of the present invention there is provided a transistor, comprising a first nanowire and a second nanowire forming a junction with the first nanowire, each of the first nanowire and the second nanowire being formed of a semiconducting material, at least partially enclosed by a nanostructure composed of a plurality of peptides, each of the plurality of peptides including no more than 4 amino acids, whereas at least one of the 4 amino acids is an aromatic amino acid; wherein the semiconducting material of the first nanowire has an n-type doping and the semiconducting material of the second nanowire has a p-type doping.

According to still a further aspect of the present invention there is provided a crossbar array, comprising a plurality of junctions each formed by a pair of crossed nanowires and at least one connector connecting the pair of crossed nanowires, the at least one connector and the pair of crossed nanowires form an electrochemical cell; wherein each of the crossed nanowires is formed of a conducting or semiconducting material, at least partially enclosed by a nanostructure composed of a plurality of peptides, each of the plurality of peptides including no more than 4 amino acids, whereas at least one of the 4 amino acids is an aromatic amino acid.

According to further features in preferred embodiments of the invention described below, the at least one connector forms a quantum state molecular switch having an electrically adjustable tunnel junction between the two nanowires.

According to still further features in the described preferred embodiments each of the plurality of junctions forms an electronic element, selected from the group consisting of a resistor, a tunneling resistor, a diode, a tunneling diode, a resonant tunneling diode and a battery.

According to still a further aspect of the present invention there is provided a device for detecting a position and/or movement of an object, the device comprising a plurality of non-intersecting nanowires, each being connected to an electronic circuitry, such that when the object contacts at least one nanowire of the plurality of non-intersecting nanowires, the at least one nanowire intersects with at least one additional nanowire of the plurality of non-intersecting nanowires, thereby allowing the electronic circuitry to generate a signal representative of the position and/or movement of an object; wherein each of, the plurality of nanowires is formed of a conducting or magnetic material at least partially enclosed by a nanostructure composed of a plurality of peptides, each of the plurality of peptides including no more than 4 amino acids, whereas at least one of the 4 amino acids is an aromatic amino acid.

According to still a further aspect of the present invention there is provided an electronic circuit assembly, comprising conductive lines being arranged in at least two layers separated therebetween by a dielectric layer, wherein conductive lines of at least a pair of layers of the at least two layers are electrically connected therebetween via at least one nanowire formed of a conducting material at least partially enclosed by a nanostructure composed of a plurality of peptides, each of the plurality of peptides including no more than 4 amino acids, whereas at least one of the 4 amino acids is an aromatic amino acid.

According to still a further aspect of the present invention there is provided a memory cell, comprising: a plurality of magnetic nanowires each formed of a ferromagnetic material at least partially enclosed by a nanostructure composed of a plurality of peptides, each of the plurality of peptides including no more than 4 amino acids, whereas at least one of the 4 amino acids is an aromatic amino acid; wherein each of the plurality of magnetic nanowires is capable of assuming two magnetization states and is connected to two conductive lines defining an address of a magnetic nanowire connected thereto.

According to further features in preferred embodiments of the invention described below, the memory cell further comprises a membrane through which the plurality of magnetic nanowires extend, wherein the two conductive lines engage opposite sides of the membrane.

According to still a further aspect of the present invention there is provided a memory cell, comprising: (a) an electrode; and (b) a nanowire, formed of a conducting material, at least partially enclosed by a nanostructure composed of a plurality of peptides, each including no more than 4 amino acids, wherein at least one of the 4 amino acids is an aromatic amino acid, the nanowire being capable of assuming one of at least two states; the nanostructure and the electrode being designed and constructed such that when electrical current flows through the electrode, the nanostructure transforms from a first state of the at least to states to a second state of the at least to states.

According to further features in preferred embodiments of the invention described below, the transformation from the first state to the second state comprises a geometrical deflection of the nanowire.

According to still a further aspect of the present invention there is provided a field emitter device, comprising an electrode and a nanowire, the electrode and the nanowire being designed and constructed such that when an electrical field is formed therebetween, electrons are emitted from the nanowire, wherein the nanowire is formed of a conducting material, at least partially enclosed by a nanostructure composed of a plurality of peptides, each including no more than 4 amino acids and wherein at least one of the 4 amino acids is an aromatic amino acid.

According to further features in preferred embodiments of the invention described below, the device further comprises a substrate having a fluorescent powder coating, the fluorescent powder coating being capable of emitting light upon activation by the electrons.

According to still a further aspect of the present invention there is provided a device for obtaining information from a nanoscale environment, the device comprising: (a) a nanowire capable of collecting signals from the nanoscale environment, the nanowire being formed of a conducting material, at least partially enclosed by a nanostructure composed of a plurality of peptides each including no more than 4 amino acids, wherein at least one of the 4 amino acids is an aromatic amino acid; and (b) a detection system capable of interfacing with the nanowire and receiving the signals thus obtaining information from the nanoscale environment; and According to further features in preferred embodiments of the invention described below, the device further comprises a supporting element onto which the nanowire being mounted, wherein the supporting element is operable to physically scan the nanoscale environment.

According to still a further aspect of the present invention there is provided an apparatus for electron emission lithography, comprising: (a) an electron emission source being at a first electrical potential, the electron emission source including at least one nanowire, each of the at least one nanowire being formed of a conducting material, at least partially enclosed by a nanostructure composed of a plurality of peptides, each including no more than 4 amino acids, wherein at least one of the 4 amino acids is an aromatic amino acid; (b) an electrically conducting mounting device being in a second electrical potential, the second electrical potential being different from the first electrical potential; wherein a difference between the second electrical potential and the first electrical potential is selected such that electrons are emitted from the electron emission source, and impinge on the mounting device to thereby perform a lithography process on a sample mounted on the mounting device.

According to further features in preferred embodiments of the invention described below, the apparatus further comprises a magnetic field generator for generating a magnetic field, thereby to direct the electrons to a predetermined location on the sample.

According to still a further aspect of the present invention there is provided a nanoscale mechanical device, comprising at least one nanostructure device designed and configured for grabbing and/or manipulating nanoscale objects, wherein the at least one nanostructure device is formed of a conducting material, at least partially enclosed by a nanostructure composed of a plurality of peptides, each including no more than 4 amino acids, wherein at least one of the 4 amino acids is an aromatic amino acid.

According to further features in preferred embodiments of the invention described below, the at least one nanostructure device comprise a first tubular nanostructure device and a second tubular nanostructure device, the first and the second tubular nanostructure devices being capable of at least a constrained motion.

According to still further features in the described preferred embodiments the device further comprises a voltage source for generating electrostatic force between the first and the second tubular nanostructure devices, thereby to close or open the first and the second tubular nanostructure devices on the nanoscale object.

According to still a further aspect of the present invention there is provided an electronic switching or amplifying device, comprising a source electrode, a drain electrode, a gate electrode and a channel, wherein at least one of the gate electrode and the channel comprises a nanowire being formed of a conducting or semiconducting material, at least partially enclosed by a nanostructure composed of a plurality of peptides, each including no more than 4 amino acids, wherein at least one of the 4 amino acids is an aromatic amino acid.

According to still a further aspect of the present invention there is provided an electronic inverter having a first switching device and a second switching device, each of the first switching device and the first switching device comprising a source electrode, a drain electrode, a gate electrode and a channel, such that the drain electrode of the first switching device is electrically communicating with the source electrode of the second switching device; wherein at least one of the gate electrode and the channel comprises a nanowire being formed of a conducting or semiconducting material, at least partially enclosed by a nanostructure composed of a plurality of peptides, each including no more than 4 amino acids, wherein at least one of the 4 amino acids is an aromatic amino acid.

According to still a further aspect of the present invention there is provided a method of emitting electrons, the method comprising forming an electric field near a nanowire, such that electrons are emitted therefrom, wherein the nanowire is formed of a conducting material, at least partially enclosed by a nanostructure composed of a plurality of peptides, each including no more than 4 amino acids, wherein at least one of the 4 amino acids is an aromatic amino acid.

According to still a further aspect of the present invention there is provided a method of obtaining information from a nanoscale environment, the method comprising: (a) collecting signals from the nanoscale environment using a nanowire, the nanowire being formed of a conducting material, at least partially enclosed by a nanostructure composed of a plurality of peptides, each including no more than 4 amino acids, wherein at least one of the 4 amino acids is an aromatic amino acid; and (b) receiving the signals from the nanowire, thus obtaining information from the nanoscale environment.

According to further features in preferred embodiments of the invention described below, the method further comprises physically scanning the nanoscale environment using the nanowire.

According to still further features in the described preferred embodiments the information signals are selected from the group consisting of mechanical signals, optical signals, electrical signals, magnetic signals, and chemical signals.

According to still further features in the described preferred embodiments the information signals comprise near field light from the nanoscale environment.

According to still further features in the described preferred embodiments the method further comprises converting physical motion of the nanowire to electric signals.

According to still a further aspect of the present invention there is provided a method of electron emission lithography, the method comprising: (a) using an electron emission source for emitting electrons, at least one nanowire, each of the at least one nanowire being formed of a conducting material, at least partially enclosed by a nanostructure composed of a plurality of peptides, each including no more than 4 amino acids, wherein at least one of the 4 amino acids is an aromatic amino acid; and (b) collecting the electrons on an electrically conducting mounting device, thereby performing a lithography process on a sample mounted on the mounting device.

According to further features in preferred embodiments of the invention described below, the method further comprises generating a magnetic field to thereby direct the electrons to a predetermined location on the sample.

According to still a further aspect of the present invention there is provided a method of recording binary information, the binary information being composed of a first type of datum and a second type of datum, the method comprising using a plurality of nanowires, each capable of assuming one of two states, wherein a first state of the two states correspond to the first type of datum and the second state of the two states correspond to the second type of datum; each of the plurality of nanowires is formed of a conducting material, at least partially enclosed by a nanostructure composed of a plurality of peptides, each including no more than 4 amino acids, wherein at least one of the 4 amino acids is an aromatic amino acid.

According to still a further aspect of the present invention there is provided a method of grabbing and/or manipulating nanoscale objects, the method comprising: (a) providing at least one nanowire, formed of a conducting material, at least partially enclosed by a nanostructure composed of a plurality of peptides, each including no more than 4 amino acids, wherein at least one of the 4 amino acids is an aromatic amino acid; and (b) using the at least one nanowire for grabbing and/or manipulating the nanoscale objects.

According to further features in preferred embodiments of the invention described below, the at least one nanowire comprise a first nanowire and a second nanowire, the first and the second nanowires being capable of at least a constrained motion.

According to still further features in the described preferred embodiments the method further comprises generating electrostatic force between the first and the second tubular nanowires, thereby closing or opening the first and the second nanowires on the nanoscale object.

According to still a further aspect of the present invention there is provided a method of cooling an object, the method comprising, (a) absorbing heat from the object using a first heat conducting layer; (b) transporting the heat away from the first heat conducting layer through a plurality of nanowires being under a potential difference; and (c) dissipating the heat over a second heat conducting layer; wherein each of the plurality of nanowires is formed of a thermoelectric material at least partially enclosed by a nanostructure composed of a plurality of peptides, and wherein each of the plurality of peptides includes no more than 4 amino acids, such that at least one of the 4 amino acids is an aromatic amino acid.

According to still further features in the described preferred embodiments the nanostructure does not exceed 500 nm in diameter.

According to still further features in the described preferred embodiments the tubular nanostructure is at least 1 nm in length.

According to still further features in the described preferred embodiments each of the 4 amino acids is independently selected from the group of naturally occurring amino acids, synthetic amino acids, β-amino acids, Peptide Nucleic Acid (PNA), and combinations thereof.

According to still further features in the described preferred embodiments at least one of the 4 amino acids is a D-amino acid.

According to still further features in the described preferred embodiments at least one of the 4 amino acids is an L-amino acid.

According to still further features in the described preferred embodiments at least one of the peptide nanostructures comprises at least two aromatic moieties.

According to still further features in the described preferred embodiments at least one of the peptide nanostructures is a homodipeptide. According to still further features in the described preferred embodiments each of the amino acids is the homodipeptide comprises an aromatic moiety, such as, but not limited to, substituted naphthalenyl, unsubstituted naphthalenyl, substituted phenyl or unsubstituted phenyl.

According to still further features in the described preferred embodiments the substituted phenyl is selected from the group consisting of pentafluoro phenyl, iodophenyl, biphenyl and nitrophenyl.

Thus, representative examples of the amino acids in the homopeptide include, without limitation, naphthylalanine, p-nitro-phenylalanine, iodo-phenylalanine and fluro-phenylalanine.

according to still further features in the described preferred embodiments the homodipeptide is selected from the group consisting of naphthylalanine-naphthylalanine dipeptide, (pentafluro-phenylalanine)-(pentafluro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

According to still further features in the described preferred embodiments the nanostructure is stable at a temperature range of 4-400° C.

According to still further features in the described preferred embodiments the nanostructure is stable in an acidic environment.

According to still further features in the described preferred embodiments the nanostructure is stable in a basic environment.

According to still further features in the described preferred embodiments the polyaromatic peptides are at least 5 amino acids in length.

According to still further features in the described preferred embodiments the polyaromatic peptides are selected from the group consisting of polyphenylalanine peptides, polytriptophane peptides, polytyrosine peptides, non-natural derivatives thereof and combinations thereof.

According to still further features in the described preferred embodiments the material is in a gaseous state.

According to still further features in the described preferred embodiments the material is in a condensed state.

According to still further features in the described preferred embodiments the material is selected from the group consisting of a conducting material, a semiconducting material, a thermoelectric material, a magnetic material, a light-emitting material, a biomineral, a polymer and an organic material.

According to still further features in the described preferred embodiments conducting material is selected from the group consisting of silver, gold, copper, platinum, nikel and palladium.

According to still further features in the described preferred embodiments, the biomineral comprises calcium carbonate.

According to still further features in the described preferred embodiments the polymer is selected from the group consisting of polyethylene, polystyrene and polyvinyl chloride.

According to still further features in the described preferred embodiments the biomolecule is selected from the group consisting of a polynucleotide and a polypeptide.

According to still further features in the described preferred embodiments the light-emitting material is selected from the group consisting of dysprosium, europium, terbium, ruthenium, thulium, neodymium, erbium, ytterbium and any organic complex thereof.

According to still further features in the described preferred embodiments the thermoelectric material is selected from the group consisting of bismuth telluride, bismuth selenide, antimony telluride, bismuth antimony telluride and bismuth selenium telluride.

According to still further features in the described preferred embodiments the magnetic material is a paramagnetic material.

According to still further features in the described preferred embodiments the paramagnetic material is selected from the group consisting of cobalt, copper, nikel and platinum.

According to still further features in the described preferred embodiments the magnetic material is a ferromagnetic material.

According to still further features in the described preferred embodiments the ferromagnetic material is selected from the group consisting of magnetite and NdFeB.

According to still further features in the described preferred embodiments the semiconducting material is selected from the group consisting of CdS, CdSe, ZnS and $SiO_2$.

The present invention successfully addresses the shortcomings of the presently known configurations by providing a peptide nanostructure encapsulating foreign materials, which can be used in various applications such as, but not limited to, electric, diagnostic, therapeutic, photonic, mechanic, acoustic and biological application.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a flowchart diagram of a method of positioning a target molecule at a predetermined location, according to a preferred embodiment of the present invention;

FIG. 2 is a flowchart diagram of a method of delivering an agent to a subject according to a preferred embodiment of the present invention;

FIG. 3 is a schematic illustration of a device for obtaining information from a nanoscale environment, according to a preferred embodiment of the present invention.

Figure 4A:
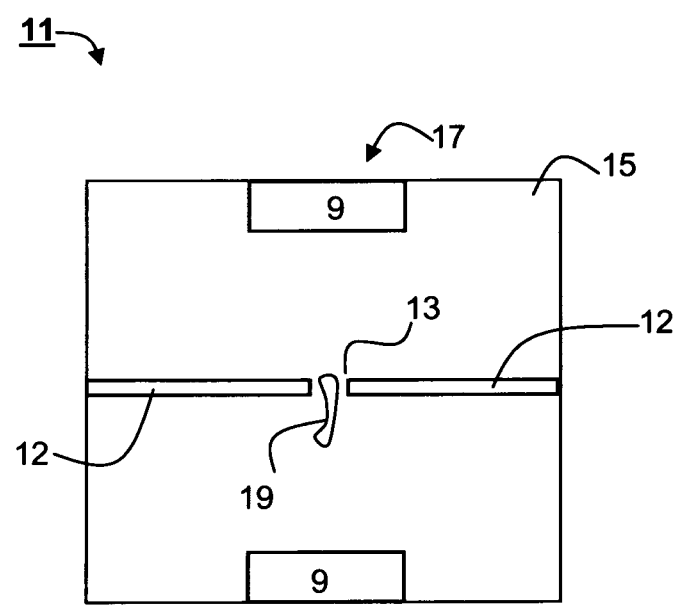
Figure 4B:
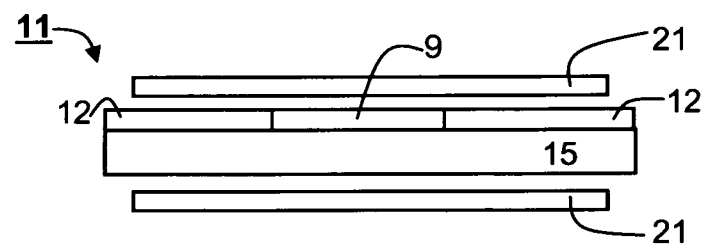
Figure 5A:
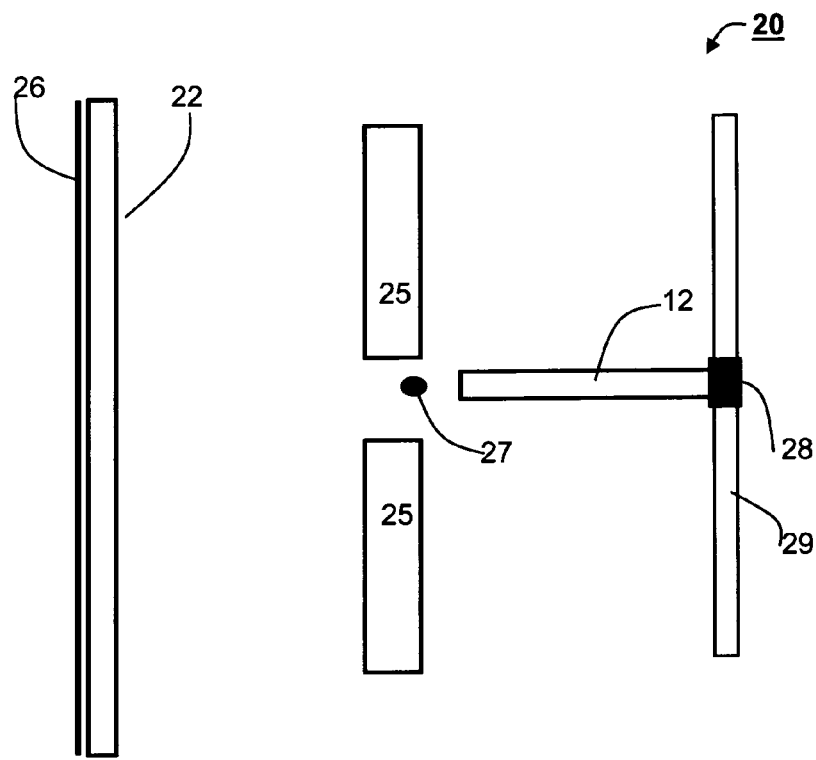

FIGS. 4a-b are schematic illustrations of a top view (FIG. 4a) and a side view (FIG. 4b) of an apparatus for characterizing a nucleic acid sequence of a polynucleotide, according to a preferred embodiment of the present invention;

FIG. 5a is a schematic illustration of a field emitter device, according to a preferred embodiment of the present invention.

Figure 5B:
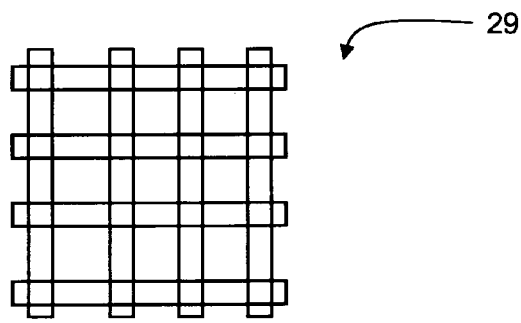

FIG. 5b is a schematic illustration of a matrix of row and column electrodes, according to a preferred embodiment of the present invention.

Figure 6:
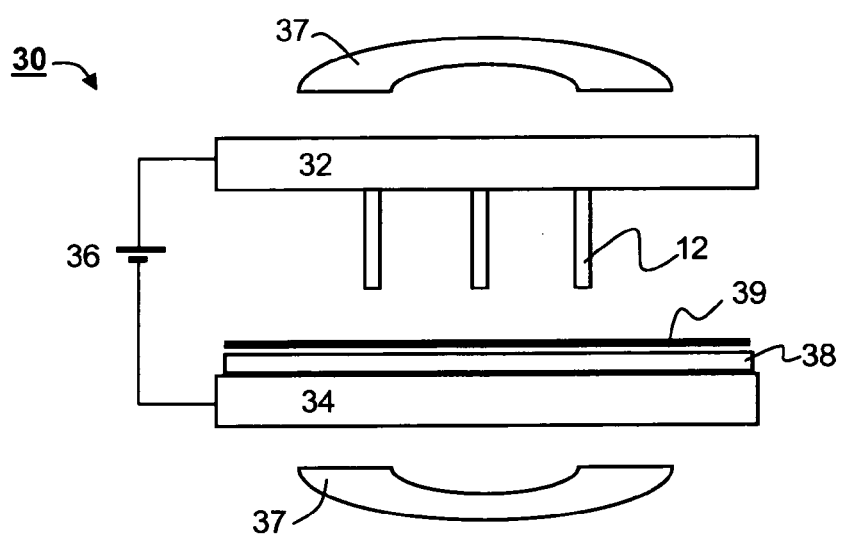

FIG. 6 is a schematic illustration of an apparatus for electron emission lithography, according to a preferred embodiment of the present invention.

Figure 7A:
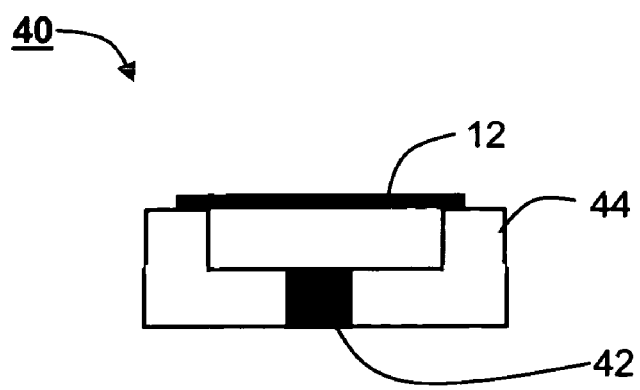
Figure 7B:
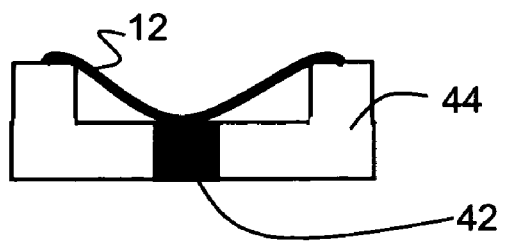

FIGS. 7a-b are schematic illustrations of a memory cell, according to a preferred embodiment of the present invention.

Figure 8:
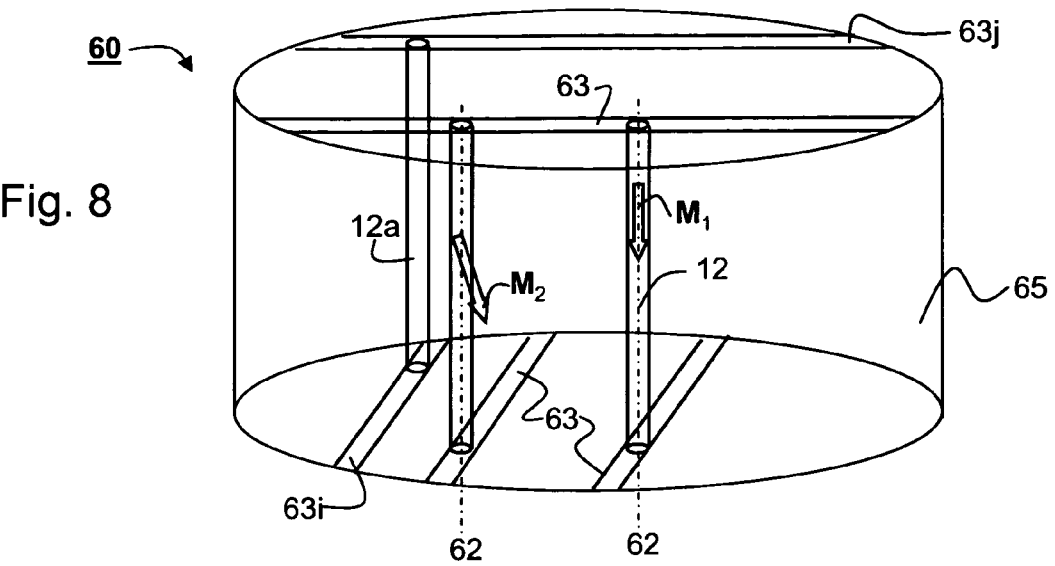
Figure 9A:
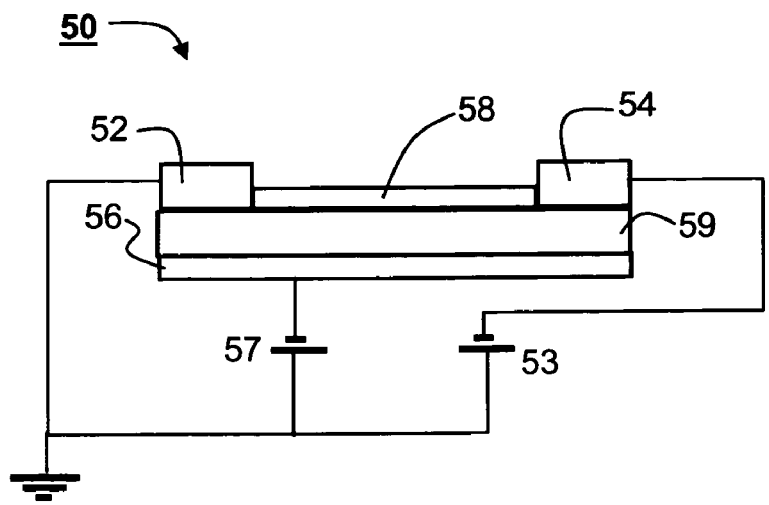

FIG. 8 is a schematic illustration of a memory cell, based on magnetic nanowires, according to a preferred embodiment of the present invention;

FIG. 9a is a schematic illustration of an electronic device for switching, inverting or amplifying, according to a preferred embodiment of the present invention.

Figure 9B:
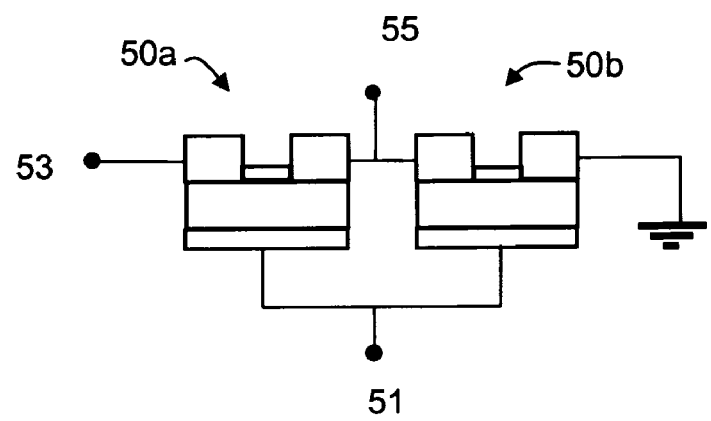

FIG. 9b is a schematic illustration of an inverter, which is formed from two devices, each similar to the device of FIG. 5a, according to a preferred embodiment of the present invention.

Figure 10A:
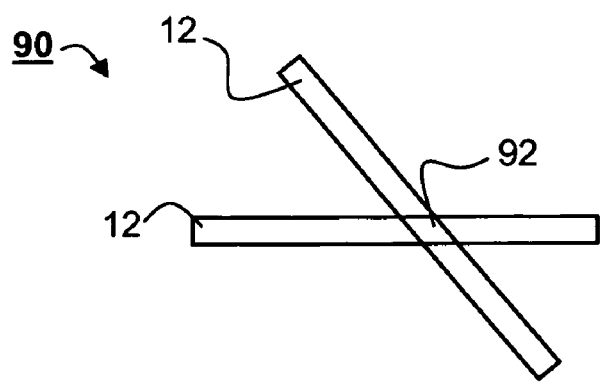
Figure 10B:
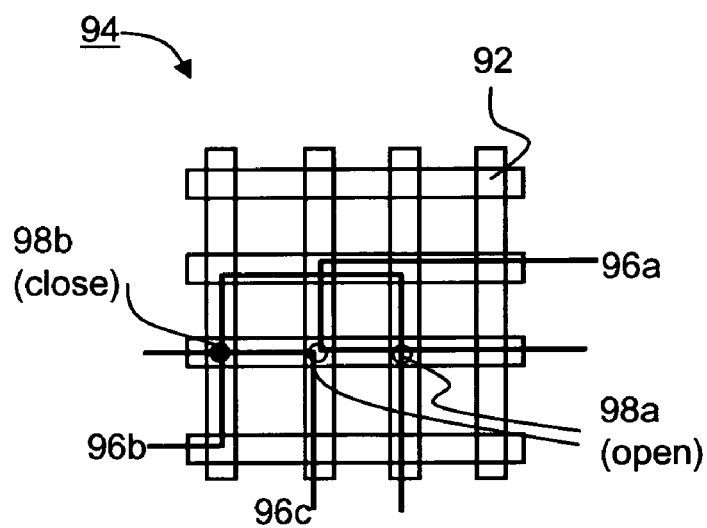
Figure 11:
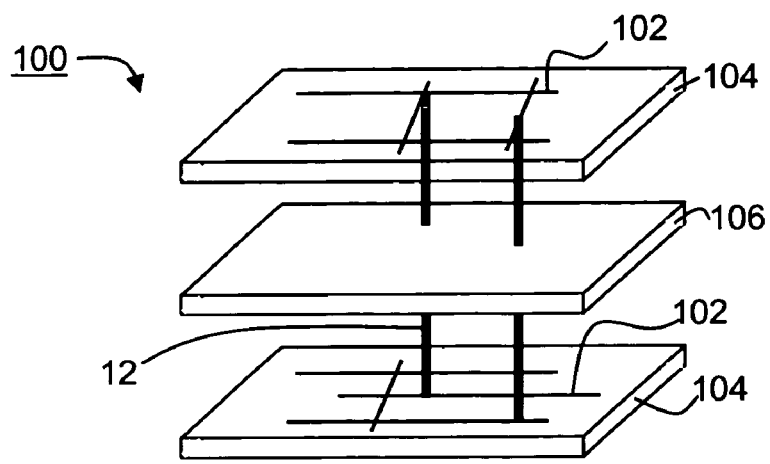
Figure 12A:
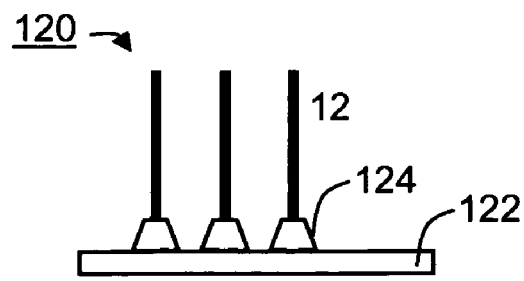
Figure 12B:
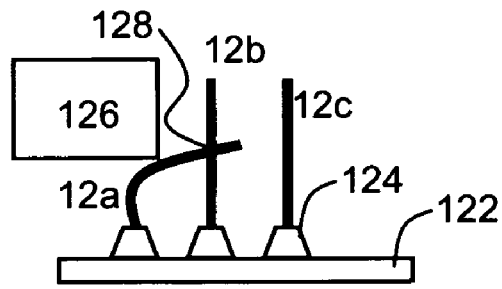
Figure 13:
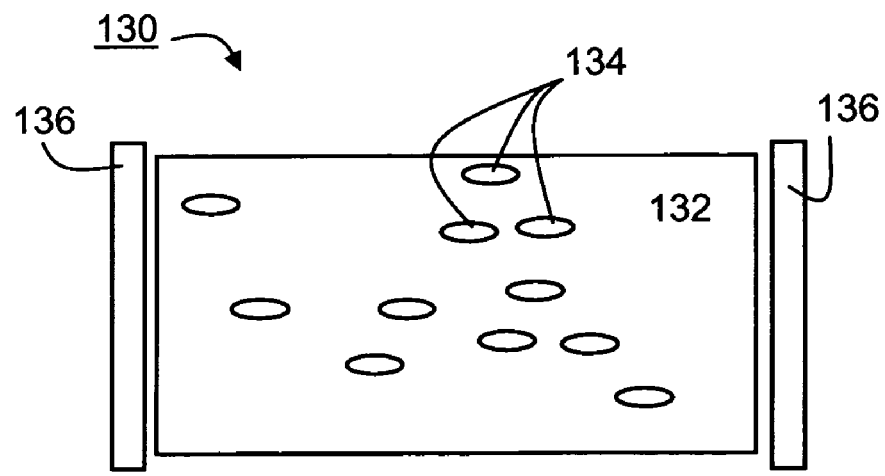
Figure 14:
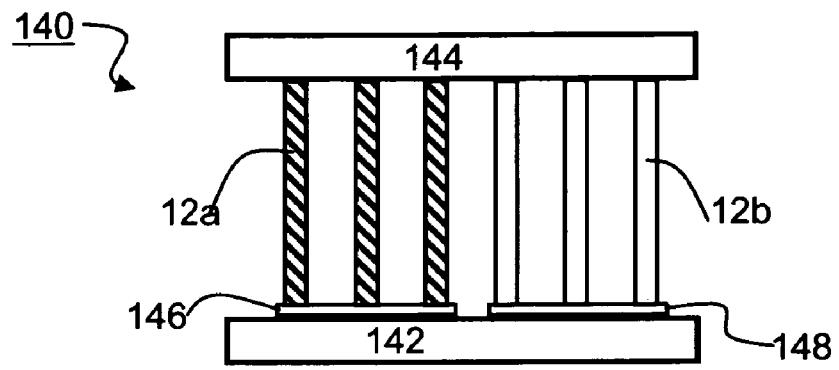
Figure 15:
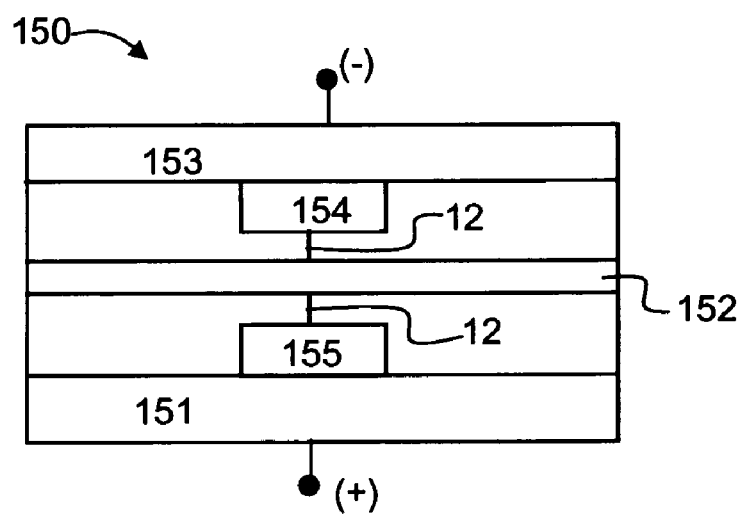
Figure 16:
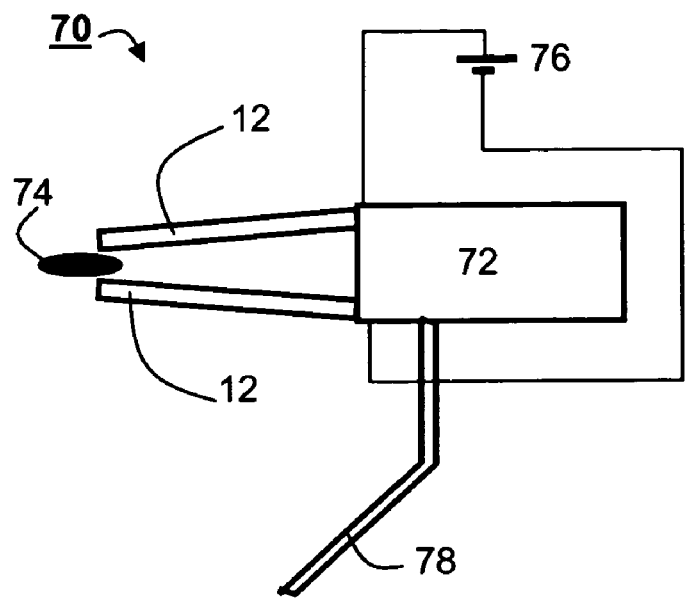

FIG. 10a is a schematic illustration of a transistor, formed of two nanowires, according to a preferred embodiment of the present invention;

FIG. 10b is a schematic illustration of an array of junctions, each defined between two nanowires, according to a preferred embodiment of the present invention;

FIG. 11 is a schematic illustration of an electronic circuit assembly, according to a preferred embodiment of the present invention;

FIGS. 12a-b are schematic illustrations of a device for detecting a position and/or movement of an object, according to a preferred embodiment of the present invention;

FIG. 13 is a schematic illustration of a display system, according to a preferred embodiment of the present invention;

FIG. 14 is a schematic illustration of a thermoelectric device, according to a preferred embodiment of the present invention;

FIG. 15 is a schematic illustration of another thermoelectric device, according to a preferred embodiment of the present invention;

FIG. 16 is a schematic illustration of a nanoscale mechanical device for griping and/or manipulating objects of nanometric size, according to a preferred embodiment of the present invention.

Figure 17:
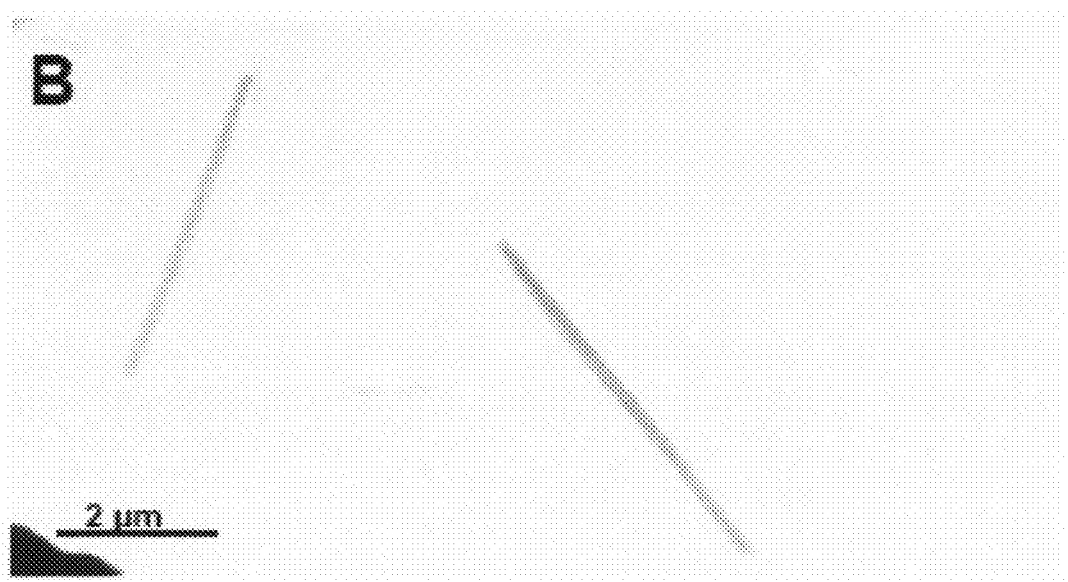

FIG. 17 is a photomicrograph depicting self-assembly of well-ordered and elongated peptide nanotubes by a molecular recognition motif derived from the β-amyloid polypeptide. The TEM image shows negatively-stained nanotubes formed by the diphenylalanine peptide.

Figure 18A:
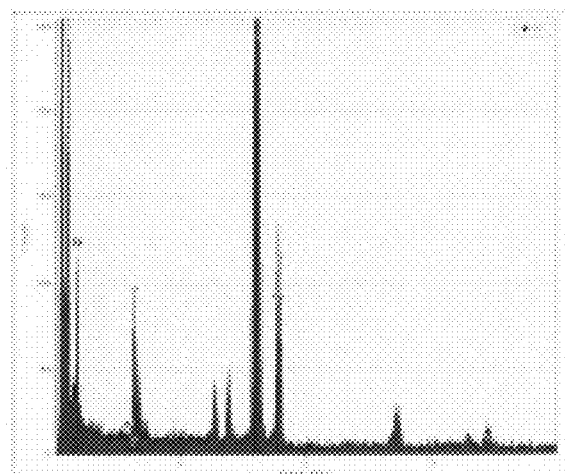
Figure 18B:
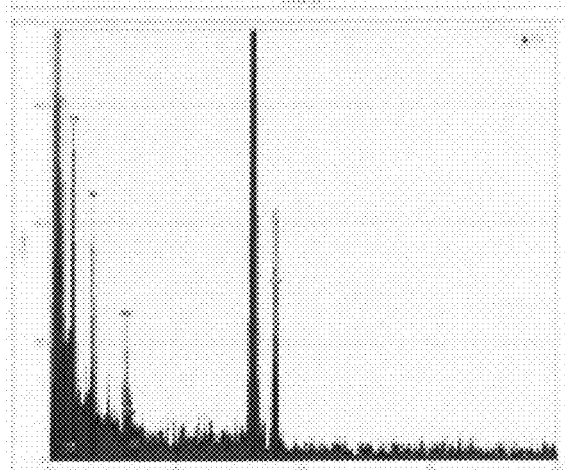
Figure 18C:
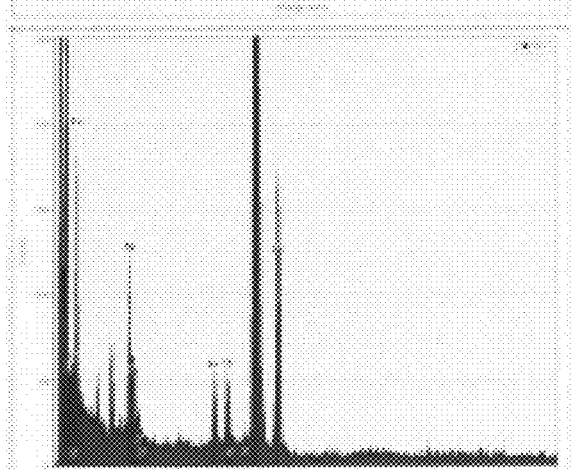

FIGS. 18a-c are graphs showing the results of Energy-dispersive x-ray analysis (EDX) on various peptide-material composites. EDX analysis was performed using a Philips Tecnai F20 Field Emission Gun—Transmission Electron Microscope (FEG-TEM) equipped with EDAX detector. FIG. 18a—shows EDX analysis effected on uranyl acetate filled peptide nanotubes. FIG. 18b—shows EDX analysis effected on silver filled peptide nanotubes. FIG. 18c—shows EDX analysis effected on Silver nanowires.

Figure 19:
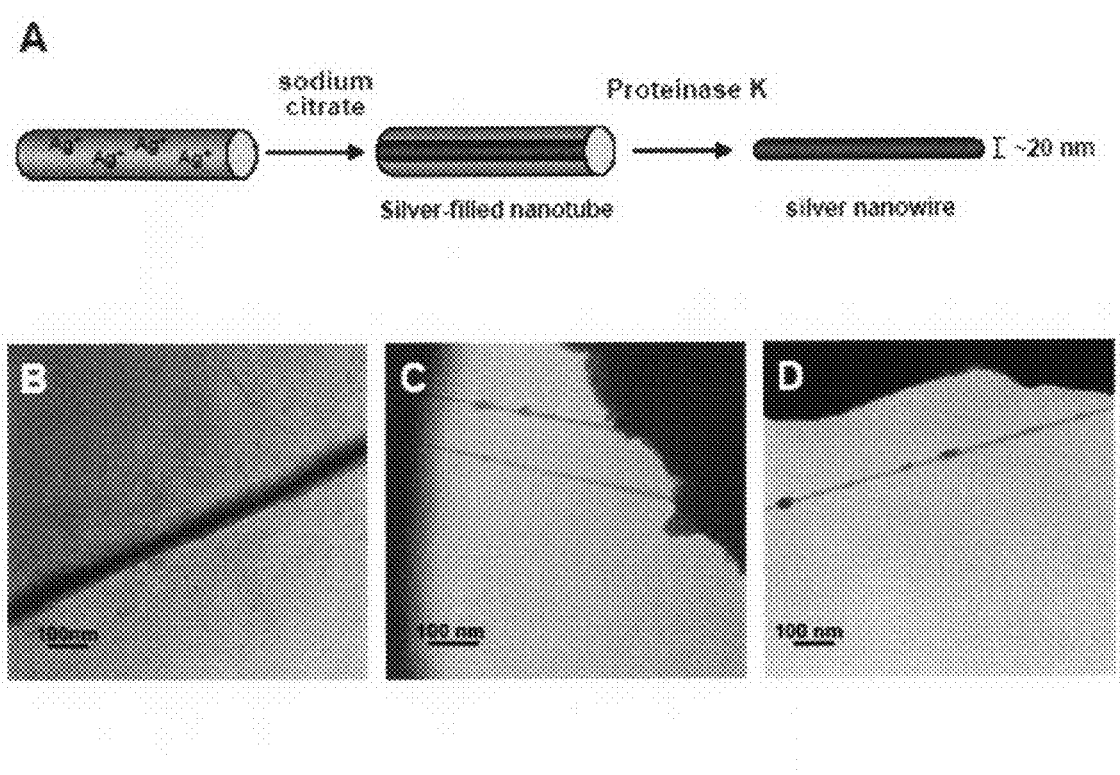

FIGS. 19a-d are photomicrographs depicting the casting of silver nanowires with the peptide nanotubes. FIG. 19a is a schematic illustration depicting the formation of a nanowire. FIG. 19b is a TEM image (without staining) of peptide tubes filled with silver nanowires. FIGS. 19c-d are TEM images of silver nanowires obtained following the addition of the Proteinase K enzyme to the nanotube solution. Size bar is indicated at the right of each image.

Figure 20:
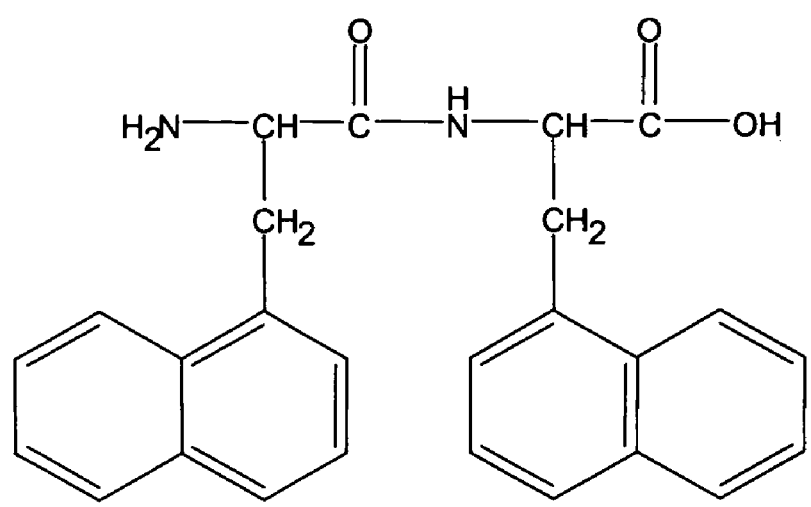

FIG. 20 is a schematic illustration of a chemical structure of a naphthylalanine-naphthylalanine (Nal-Nal) dipeptide.

Figure 21:
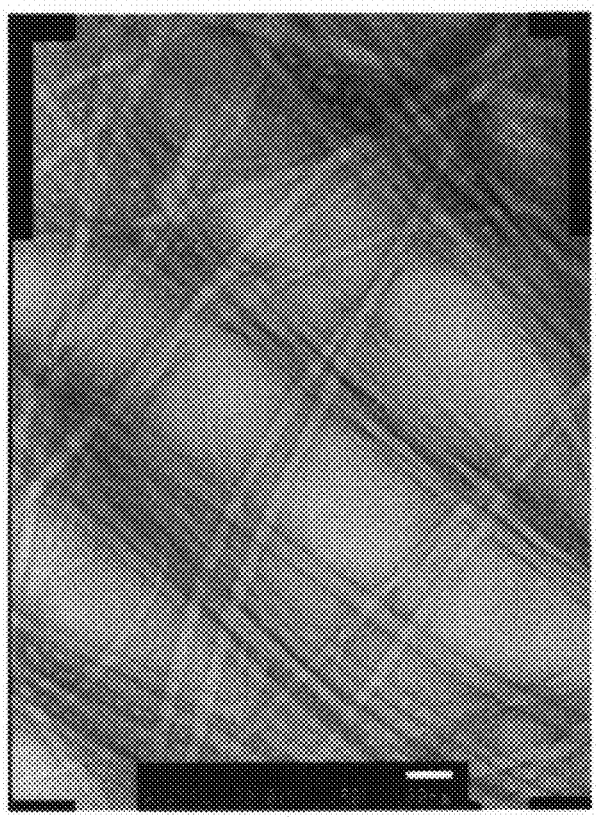

FIG. 21 is an electron microscope image of Nal-Nal tubular-nanostructures.

Figure 22A:
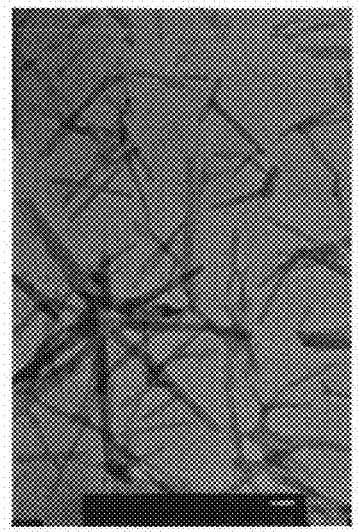
Figure 22B:
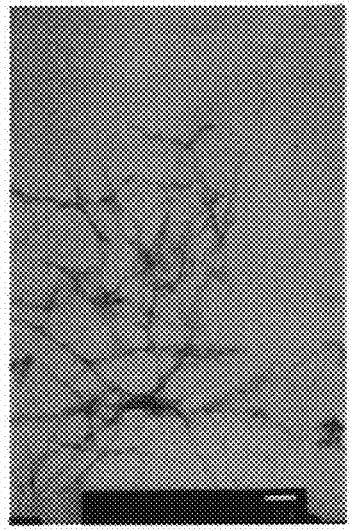
Figure 22C:
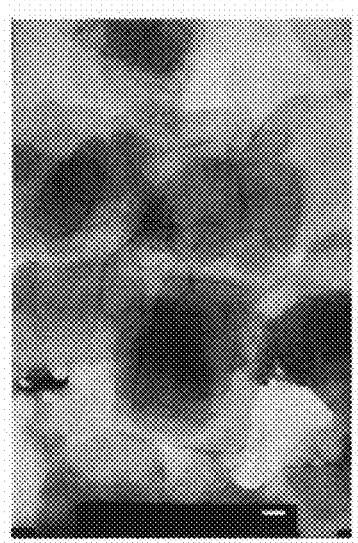
Figure 22D:
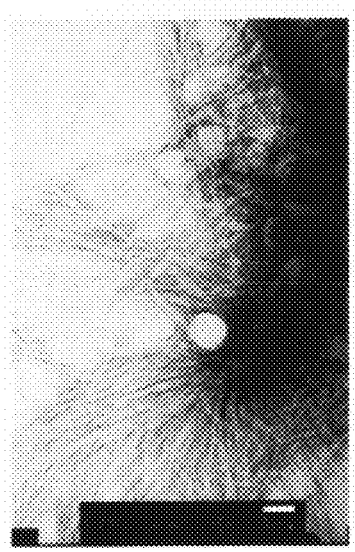

FIGS. 22A-D are electron microscope images of tubular and planar nanostructures assembled from the following aromatic-homodipeptides: (Pentafluro-phenylalanine)-(pentafluro-phenylalanine) (FIG. 22A), (iodo-phenylalanine)-(iodo-phenylalanine) (FIG. 22B), (4-phenyl phenylalanine)-(4-phenyl-phenylalanine) (FIG. 22C), and (p-nitro-phenylalanine)-(p-nitro-phenylalanine) (FIG. 22D).

DESCRIPTION OF THE PREFERRED EMBODIMENTS

The present invention is of a peptide nanostructure encapsulating foreign materials. Specifically, the present invention can be used in numerous applications, such as, but not limited to, field effect transistors, bipolar transistors, complementary inverters, tunnel diodes, light emitting diodes, sensors, display systems and devices, memory chips, cooling systems, nano-mechanical devices and the like. The peptide nanostructure can also be used in numerous medical and biological applications, such as, but not limited to, drug delivery, molecule monitoring and locomotion, nucleic acid sequencing and the like.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Self-assembled nanostructures allow controlled fabrication of novel nanoscopic materials and devices. Nanotubular structures are particularly important as they may serve as nanowires and nanoscaffolds in numerous applications. Most widely used nanotubes are made of carbon or peptide assemblers (i.e., building blocks). While carbon nanotubes, suffer from major structural defects including branching and bending resulting in spatial structures with unpredictable electronic, molecular and structural properties, peptide nanotubes such as those composed of surfactant like peptides and cyclic D-, L-peptide subunits form crystals, networks, or bundles of nanostructures and thus can not be used in the above-described applications.

While reducing the present invention to practice, the present inventors uncovered that aromatic peptides (e.g., diphenylalanine) are capable of forming tubular and spherical nanostructures, which can be used in numerous mechanical, electrical, chemical, optical and biotechnological systems.

Although the term nanotubes was previously attributed to hollow nanometric channels, which are formed within the macroscopic crystal structure of diphenylalanine peptides [Gorbitz (2001) Chemistry 38:6791] these so called 'nanotubes' are structurally different from the individual nanostructures formed by the present invention.

The difference in structure can be explained by the different conditions which were used to assemble the structures. While Gorbitz allowed crystallization by evaporation of an aqueous peptide solution in high temperature (i.e., 80° C.), the present inventors allowed self-assembly in an aqueous solution under mild-conditions (see Example 1 of the Examples section which follows).

Thus, according to one aspect of the present invention, there is provided a tubular, spherical or planar nanostructure. The nanostructure of this aspect of the present invention is composed of a plurality of peptides, each peptide including no more than 4 amino acids of which at least one is an aromatic amino acid.

As used herein the phrase "tubular, spherical or planar nanostructure" refers to a planar (e.g., disk-shape), spherical or elongated tubular or conical structure having a diameter or a cross-section of less than 1 μm (preferably less than 500 nm, more preferably less than about 50 nm, even more preferably less than about 5 nm). The length of the tubular nanostructure of the present invention is preferably at least 1 μm, more preferably at least 10 nm, even more preferably at least 100 nm and even more preferably at least 500 nm. It will be appreciated, though, that the tubular structure of the present invention can be of infinite length (i.e., macroscopic fibrous structures) and as such can be used in the fabrication of hyper-strong materials.

The nanostructure of the present invention is preferably hollow and can be either conductive, semi-conductive or non-conductive.

According to a preferred embodiment of this aspect of the present invention the peptide is a dipeptide or a tripeptide such as set forth in SEQ ID NO: 1, 5, 6, 7 or 8 (see the Examples section which follows). Depending on the rigidity of the molecular structure of the peptide used, tubular or spherical nanostructures are formed. Thus, for example a plurality of diphenylglycine peptides, which offer similar molecular properties as diphenylalenine peptides albeit with a lower degree of rotational freedom around the additional C—C bond and a higher steric hindrence will self-assemble into nano spheres, while a plurality of diphenylalenine peptides will self-assemble into nanotubes.

The present invention also envisages nanostructures which are composed of a plurality of polyaromatic peptides being longer than the above described (e.g., 50-136 amino acids).

As used herein the phrase "polyaromatic peptides" refers to peptides which include at least 80%, at least 85% at least 90%, at least 95% or more, say 100% aromatic amino acid residues. These peptides can be homogenic (e.g., polyphenylalanine, see Example 3 of the Examples section which follows) or heterogenic of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 120, at least 125, at least 130, at least 135, at least 140, at least 145, at least 150, at least 155, at least 160, at least 170, at least 190, at least 200, at least 300, at least 500 amino acids.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2—NH, CH2—S, CH2—S=O, O=C—NH, CH2—O, CH2—CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N (CH3)—CO—), ester bonds (—C(R)H—C—O—O—C (R)—N—), ketomethylen bonds (—CO—CH2—), α-aza bonds (—NH—N(R)—CO—), wherein R is, any alkyl, e.g., methyl, carba bonds (—CH2—NH—), hydroxyethylene bonds (—CH(OH)—CH2—), thioamide-bonds (—CS—NH—), olefinic double bonds (—CH=CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylalanine (Nal), ring-methylated derivatives of Phe, halogenated derivatives of Phe or o-methyl-Tyr, and β amino-acids.

In addition to the above, the peptides of the present invention may also include one or more modified amino acids (e.g., thiolated amino acids, see Example 2 of the Examples section, or biotinylated amino acids) or one or more non-amino acid monomers (e.g. fatty acids, complex carbohydrates etc). Also contemplated are homodipeptides, and more preferably aromatic homodipeptides in which each of the amino acids comprises an aromatic moiety, such as, but not limited to, substituted or unsubstituted naphthalenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydro furane, tetrahydropyrane, morpholino and the like.

A "hydroxy" group refers to an —OH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to an —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

Representative examples of such homodipeptides include, without limitation, a naphthylalanine-naphthylalanine (Nal-Nal) dipeptides (SEQ ID NO: 9), (pentafluro-phenylalanine)-(pentafluro-phenylalanine) (SEQ ID NO: 10), (iodo-phenylalanine)-(iodo-phenylalanine) (SEQ ID NO: 11), (4-phenyl phenylalanine)-(4-phenyl phenylalanine) (SEQ ID NO: 12) and (p-nitro-phenylalanine)-(p-nitro-phenylalanine) (SEQ ID NO: 13) (see Example 4-5 and FIGS. 20-22).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |

TABLE 2-continued

| Non-conventional amino acid | Code | Non-conventional amino acid | Code |
|---|---|---|---|
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
| --- | --- | --- | --- |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenyleth-yl)carbamylmethyl-glycine | Nnbhm | N-(N-(3,3-diphenylprop-yl)carbamylmethyl(1)glycine | Nnbhe |
| 1-carboxy-1-(2,2-diphenyl-ethylamino)cyclopropane | Nmbc | | |

The nanostructures of the present invention are preferably generated by allowing a highly concentrated aqueous solution of the peptides of the present invention to self-assemble under mild conditions as detailed in the Examples section which follows.

The resulting nanostructures are preferably stable under acidic and/or basic pH conditions, a wide range of temperatures (e.g., 4-400° C., more preferably, 4-200° C.) and/or proteolytic conditions (i.e., proteinase K).

According to preferred embodiments of the present invention, the nanostructures are filled or partially filled with at least one material (i.e., the nanostructure enclose or partially enclose the material).

The material can be composed of a conducting material, a semiconducting material, a thermoelectric material, a magnetic material (paramagnetic, ferromagnetic or diamagnetic), a light-emitting material, a gaseous material, a biomineral, a polymer and/or an organic material.

For example, the nanostructures may enclose conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the nanostructures may enclose, for example, silver, gold, copper, platinum, nickel, or palladium. For semiconducting materials the nanostructures may enclose, for example, silicon, indium phosphide, gallium nitride and others.

The nanostructures may also encapsulate, for example, any organic or inorganic molecules that are polarizable or have multiple charge states. For example, the nanostructures may include main group and metal atom-based wire-like silicon, transition metal-containing wires, gallium arsenide, gallium nitride, indium phosphide, germanium, or cadmium selenide structures.

Additionally, the nanostructure of the present invention may enclose various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

Specific and representative examples of semiconducting materials which can be encapsulated by the nanostructure of the present invention include, without limitation, CdS, CdSe, ZnS and SiO$_2$.

The nanostructure of the present invention may also enclose a thermoelectric material that exhibits a predetermined thermoelectric power. Preferably, such a material is selected so that the resulting nanostructure composition is characterized by a sufficient figure of merit. Such composition, as further detailed hereinunder, may be used in thermoelectric systems and devices as heat transfer media or thermoelectric power sources. According to a preferred embodiment of the present invention the thermoelectric material which can be encapsulated in the nanostructure of the present invention may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like. Other materials are disclosed, for example, in U.S. Patent Application No. 20020170590.

As stated, the nanostructure of the present invention may also enclose magnetic materials. Generally, all materials in nature posses some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by the nanostructure of the present invention include, without limitation, cobalt, copper, nickel, and platinum. Representative examples of ferromagnetic materials include, without limitation, magnetite and NdFeB.

Other materials which may be encapsulated by the nanostructure of the present invention include, without limitation, light-emitting materials (e.g., dysprosium, europium, terbium, ruthenium, thulium, neodymium, erbium, ytterbium or any organic complex thereof), biominerals (e.g., calcium carbonate) and polymers (e.g., polyethylene, polystyrene, polyvinyl chloride, polynucleotides and polypeptides).

In order to generate the filled nanostructure of the present invention, the foreign material is introduced into the internal cavity of the tubular or spherical nanostructure, to encapsulate the material in nanostructure.

A method of filling is described in the Example section which follows, exhibiting casting of nanowires, using as a mold, the nanotubes of the present invention.

Other methods of filling nanotubes are described in "Capillarity-induced filling of carbon nanotubes", P M Ajayan et al., Nature, vol. 361, 1993, pp. 333-334; "A simple chemical method of opening and filling carbon nanotubes", S C Tsang et al., Nature, vol. 372, 1994, pp. 159-162; U.S. Pat. Nos. 5,916,642 and 6,361,861.

Filled nanostructures can be used as such (as further described hereinbelow), Alternatively, the peptide mold (i.e., nanotube or nanosphere of the present invention), can be removed such as by using a protease (as further described in the Examples section), to increase properties of the casted material, such as conductivity.

Hence, depending on the foreign material present in (encapsulated in) and/or around (coated on, as further described hereinbelow) the nanostructure of the present invention, the peptide nanostructure can be an insulator, a conductor, a semiconductor, thermoelectric, magnetic and the like. The nanostructure of the present invention can also be utilized as vehicles in which atoms of different materials (e.g., conducting, semiconducting, magnetic, thermoelectric, chemical or biological agents) may be enclosed, either in a condensed or in a gaseous state.

A detailed description of the nanostructure generated according to the teachings of the present invention follows below, starting first with a description of the applications of such nanostructures and the advantages offered thereby.

Generally, the nanostructures of the present invention can be used in various applications which involve the use of nanoscopic elements. Such applications are known in the art and disclosed in U.S. Pat. Nos. 5,581,091, 6,383,923, 6,426,134, 6,428,811, 6,428,811, 6,504,292, 6,530,944, 6,559,468, 6,579,742, 6,586,095, 6,628,053 and in U.S. Patent Application Nos. 20020053257, 20020054461, 20020175618, 20020180077, 20020187504, 20030089899, 20030096113, 20030121764, 20030141189, 20030165074, 20030180491 and 20030197120, which are incorporated herein by reference.

The nanostructure of the present invention has numerous potential applications. Having a substantially high aspect ratio, the nanostructure of the present invention is an ideal candidate for use in probing application. For example, a nanostructure having a tip diameter of about 10 nm and a length of several micrometers can be used as the tip of an atomic force microscope to probe deep crevices found on integrated circuits, biological molecules or any other nanoscale environment.

Additionally, the nanostructure of the present invention can be used in the field of micro- and sub-microelectronic circuitry and devices. More particularly, nanostructure of the present invention can be feature nanoscale wires, referred to herein as nanowires, which can be selectively doped at various locations. The nanowires can be doped, for example, differentially along their length, or radially, and either in terms of identity of dopant, concentration of dopant, or both. This may be used to provide both n-type and p-type conductivity in a single item, or in different items in close proximity to each other, such as in a crossbar array.

The nanostructure of the present invention can be combined with silicon chips so as to restrict motion of electrons or holes within a nanoscale region thereby to provide the system with special electric, optical and/or chemical characteristics. For example, the use of nanostructure as gates in an electronic device allows operation at low gate voltage and enables the switching of several individual devices on the same substrate.

Devices and systems incorporating the nanostructures of the present invention may be controlled, for example, using any input signal, such as an electrical, optical or a magnetic signal. The control may involve switching between two or more discrete states or may involve continuous control of a nanowire current, i.e., analog control. In addition to electrical signals, optical signals and magnetic signals, the devices may also be controlled in certain embodiments in response to biological and chemical species, for example, DNA, protein, metal ions. In a more general sense, the nanostructures of the present invention may be charged or have a dipole moment. In other embodiments, the device may be switchable in response to mechanical stimuli, for example, mechanical stretching, vibration and bending. In yet other embodiments, the device may be switchable in response to temperature, pressure or fluid movement, for example, the movement of an environmental gas or liquid.

Following are representative examples of applications in which the nanostructure of the present invention is preferably incorporated.

Figure 1:
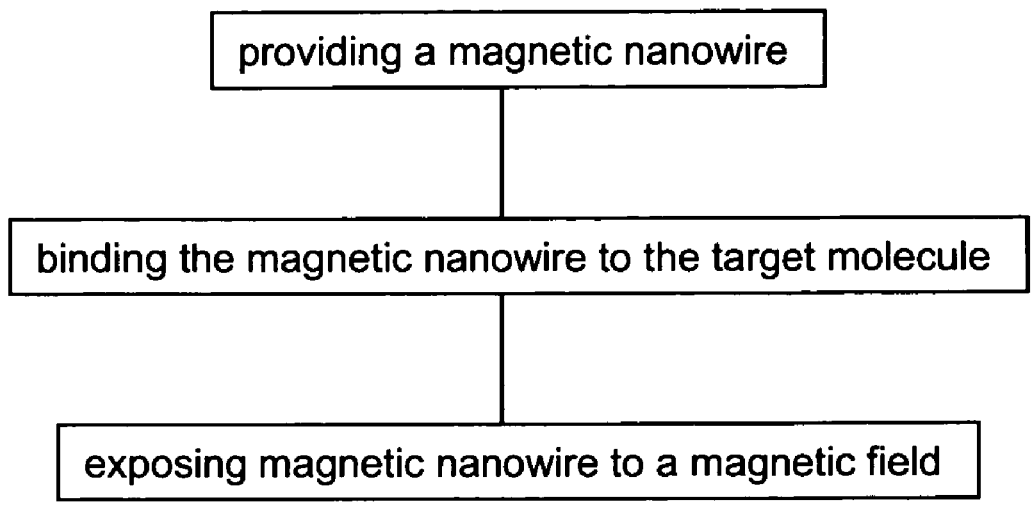

Referring now to the drawings, FIG. 1 is a flow chart diagram of a method of positioning a target molecule at a predetermined location. The method comprises the following method steps in which in a first step, a magnetic nanowire is provided. The magnetic nanowire is preferably formed of a magnetic material at least partially enclosed by the peptide nanostructure of the present invention. According to a preferred embodiment of the present invention, the nanostructure has at least one segment associated with a functional group or ligand, which are capable of binding to the target molecule.

Representative examples of functional groups which are contemplated include, without limitation, thiols, disulfides, cyanides, amines, carboxylic acids, phosphonates, siloxanes or hydroxamic acids. Representative examples of ligands which are contemplated include, without limitation, proteins, fibronectin, DNA, RNA, enzymes, ribozymes, hydrophobic materials, hydrophillic materials, cells, tissue, microorganisms, bacteria, viruses and chemoattractant.

In a second step of the method, the magnetic nanowire is bound to the target molecule, and in the third step, the magnetic nanowire (and the target molecule to which it bounds) is exposed to a magnetic field. As stated, when a magnetic material is placed in a magnetic field, its magnetic properties are manifested by forces acting thereon. Thus, by a judicious selection of the magnetic field (magnitude and direction) the nanowire, under the influence of the magnetic force, may be moved, together with the target molecule, to the desired location.

According to another aspect of the present invention, there is provided a method of delivering an agent to a subject. The method comprises the following method steps which are illustrated in the flowchart diagram of FIG. 2.

Figure 2:
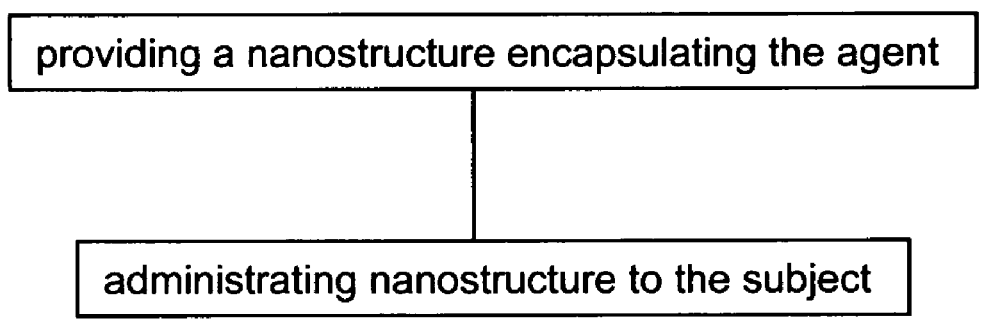

Referring to FIG. 2, in a first step of the method, a composition having the agent enclosed by the peptide nanostructure of the present invention is provided, and in a second step, the nanostructure is administrated to the subject. The present aspect of the invention has numerous, of potential application in the field of drug delivery, DNA transfection, and other medical and biological applications. The nanostructure of the present invention has a particular advantage for these applications because of its low toxicity, biodegradability.

In this respect, according to a preferred embodiment of the present invention the composition may further comprise one or more functional groups. In one embodiment, the functional group is an antigen-binding moiety, by which is meant a moiety comprising the antigen-recognition site of an antibody. Examples of a moiety comprising the antigen-recognition site of an antibody include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies. Single chain or multiple chain antigen-recognition sites can be used. Multiple chain antigen-recognition sites, can be fused or unfused.

The antigen-binding moiety can be selected from any known class of antibodies. Known classes of antibodies include, but are not necessarily limited to, IgG, IgM, IgA, IgD, and IgE. The various classes also can have subclasses. For example, known subclasses of the IgG class include, but are not necessarily limited to, IgG1, IgG2, IgG3, and IgG4. Other classes have subclasses that are routinely known by one of ordinary skill in the art.

The antigen-binding moiety can be selected from an antibody derived from any species. "Derived from," in this context, can mean either prepared and extracted in vivo from an individual member of a species, or prepared by known biotechnological techniques from a nucleic acid molecule encoding, in whole or part, an antibody peptide comprising invariant regions which are substantially identical to antibodies prepared in vivo from an individual member of the species or an antibody peptide recognized by antisera specifically, raised against antibodies from the species. Exemplary species include, but are not limited to, human, chimpanzee, baboon, other primate, mouse, rat, goat, sheep, and rabbit, among others known in the art. In one, embodiment, the antibody is chimeric, i.e., comprises a plurality of portions, wherein each portion is derived from a different species. A chimeric antibody, wherein one of the portions is derived from human, can be considered a humanized antibody.

Antigen-recognition moieties are available that recognize antigens associated with a wide variety of cell types, tissues, and organs, and a wide variety of medical conditions, in a wide variety of mammalian species. Exemplary medical conditions include, but are not limited to, cancers, such as lung cancer, oral cancer, skin cancer, stomach cancer, colon cancer, nervous system cancer, leukemia, breast cancer, cervical cancer, prostate cancer, and testicular cancer; arthritis; infections, such as bacterial, viral, fungal, or other microbial infections; and disorders of the skin, the eye, the vascular system, or other cell types, tissues, or organs.

When the nanostructure of the present invention encapsulates a conducting material, a nanowire is formed. Such a nanowire can be used as an interface between macroscopic systems and individual objects having nanometer dimensions.

Hence, further in accordance with the present invention there is provided a device for obtaining information from a nanoscale environment. The device according to this aspect of the present invention may comprise one or more nanostructures encapsulating a conducting material, which facilitate information exchange between the macroscopic system and the nanoscale environment. Individual nanostructures, nanowires or bundles thereof can be recovered from peptides; as further detailed hereinabove, in accordance with the present invention. Assemblies of nanostructures can be fabricated, for example, by self-assembly of groups of nanostructures, as further detailed and exemplified in the Examples section that follows.

Figure 3:
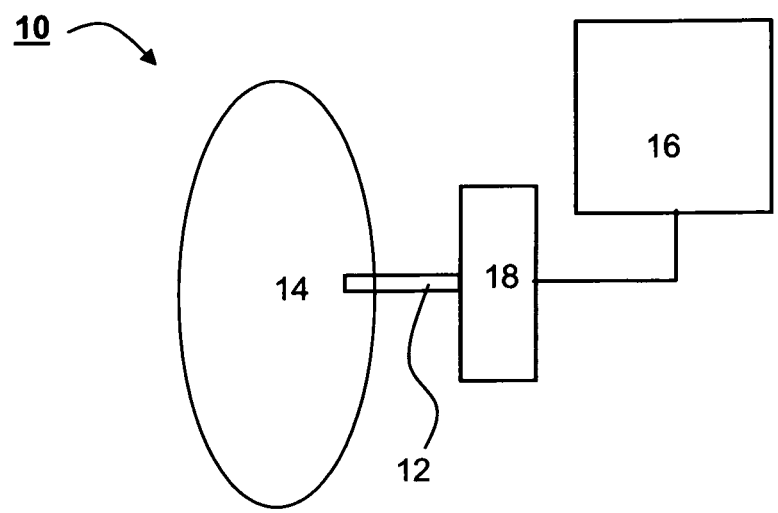

Referring now to the drawings, FIG. 3 is a schematic illustration of the device described above, which is referred to herein as device 10. In its most basic form, device 10 comprises a nanowire 12 encapsulating a conducting material (e.g., a nanowire) and a detection system 16.

Nanowire 12 serves for collecting signals from a nanoscale environment 14. Any type of signals can be collected by nanowire 12 including, without limitation, mechanical, optical, electrical, magnetic and chemical signals. Detection system 16 serves for interfacing with nanowire 12 and receiving the signals collected thereby. Hence, by collecting signals using nanowire 12 and detecting the signals using system 16, device 10 is capable of sensing, measuring and analyzing nanoscale environment 14.

According to a preferred embodiment of the present invention device 10 may further comprise a supporting element 18 onto which nanowire 12 is mounted. Nanowire 12 is connected to supporting element 18 at one end, with the other end being free and, due to its nanometric dimension, capable of coming into direct contact or near proximity to nanoscale environment 14. Preferably, supporting element 18 can physically scan nanoscale environment 14 to thereby allow nanowire 12 to collect signals from, or deliver signals to a plurality of locations of nanoscale environment 14. The "sensing end" of nanowire 12 interacts with objects being sensed, measured or analyzed by means which are (either individually or in combination) physical, electrical, chemical, electromagnetic or biological. This interaction produces forces, electrical currents or chemical compounds which reveal information about the object.

Nanowire 12 and supporting element 18 in combination can essentially be considered as a transducer for interacting with nanoscale environment 14. Conventional probe microscopy techniques are enabled and improved by the use of device 10, according to a preferred embodiment of the present invention.

Examples of conventional systems of this type include scanning tunneling microscopes, atomic force microscopes, scanning force microscopes, magnetic force microscopes and magnetic resonance force microscopes.

Device 10 is fundamentally different from conventional probe microscopy tips in its shape and its mechanical, electronic, chemical and/or electromagnetic properties. This difference permits new modes of operation of many probe microscopes, and new forms of probe microscopy. Device 10 is capable of imaging, at nanoscale resolution or greater, surfaces and other substrates including individual atoms or molecules such as biolmolecules. Device, 10 can replace relevant parts (e.g., tips) of any of the above systems.

In a preferred embodiment, supporting element 18 and/or nanowire 12 may be pre-coated with a layer of conductive material in order to produce a good electrical contact therebetween.

Device 10 is particularly useful when used in tapping mode atomic force microscopy. In this mode, a change in amplitude of an oscillating cantilever driven near its resonant frequency is monitored as nanowire 12 taps the surface of nanoscale environment 14. The sharp frequency response of high-quality cantilevers makes this technique exquisitely sensitive. Nanostructure 14 has the advantage that it is both stiff below a certain threshold force, but is compliant above that threshold force. More specifically, below the Euler buckling force, there is no bending of nanowire 12. The Euler buckling force of nanowire 12 is preferably in the one nano-Newton range. Once the Euler bucking force is exceeded, nanowire 12 bends easily through large amplitudes with little additional force. In addition, nanowire 12 is extremely gentle when laterally touching an object.

The result is that gentle, reliable atomic force microscopy imaging may be accomplished in the tapping mode with even extremely stiff, high-resonant frequency cantilevers. In contrast to the hard silicon pyramidal tip of existing systems, which can easily generate impact forces being larger than 100 nano-Newtons per tap, and therefore may, substantially modify the geometry of soft samples such as large bio-molecules, nanowire 12 serves as a compliant probe which moderates the impact of each tap on the surface.

An additional advantage of device 10 is its capability to explore regions of nanoscale environment 14 previously inaccessible to high resolution scanning probes. In this embodiment, nanowire 12 is preferably of tubular shape so as to allow nanowire 12 to penetrate into deep trenches of environment 14. Due to the above mention special mechanical characteristics of nanowire 12 scanning force microscopy imaging of tortuous structures can be, achieved without damaging nanowire 12 or the imaged object.

Device 10 of the present invention can also be utilized to retrieve other types of information from nanoscale environment 14, such as, but not limited to, information typically obtained via conventional friction force microscopy. Friction force microscopy measures the atomic scale friction of a surface by observing the transverse deflection of a cantilever mounted probe tip. The compliance of nanowire 12 above the Euler threshold as described above, provides for a totally new method of elastic force microscopy. By calibration of the Euler buckling force for nanowire 12, and making appropriate atomic force microscopy measurements using nanowire 12, one can obtain direct information about the elastic properties of the object being imaged.

Device 10 may also be used to perform nanoscale surface topography measurement. Motions of supporting element 18 can be calibrated by measurement of surfaces having known geometries (e.g., pyrolytic graphite with surface steps). Once properly calibrated, supporting element 18 and nanowire 12 can provide precise measurement of the topography of surfaces and fabricated elements such as vias and trenches on integrated-circuit elements.

An additional use of device 10 is in mechanical resonance microscopy, which can be facilitated by mechanical resonances in nanowire 12. These resonances may be utilized as a means of transduction of information about the object being sensed or modified. Such resonances, as will be known by one skilled in the art, can be sensed by optical, piezoelectric, magnetic and/or electronic means.

Nanowire 12 can also act as a sensitive antenna for electromagnetic radiation. The response of nanowire 12 to electromagnetic radiation may be recorded by detecting and measuring frequency currents passing therethrough as it and the object being sensed interact together in a nonlinear way with electromagnetic radiation of two or more frequencies. Via its interaction with electromagnetic fields of specified frequencies, nanowire 12 may excite electronic, atomic, molecular or condensed-matter states in the object being examined, and the transduction of information about that object may occur by observation of the manifestations of these states.

Also of interest is the use of device 10 for probing biological systems. For example, device 10 can perform DNA sequencing by atomic force microscopy imaging of DNA molecules whereby nanowire 12, due to its physical and chemical properties, permits the recognition of individual bases in the molecule. An additional apparatus for polynucleotide sequencing is further described in more details hereinafter.

In another biological application, device 10 can also be used for electrical or electrochemical studies of living cells. Knowledge of cell activity can be achieved e.g., by measuring and recording electrical potential changes occurring within a cell. For example, device 10 of the present inventions can accurately monitor specific cytoplasmic ions and cytosolic calcium concentrations with a spatial resolution far superior to those presently available. Living cells which can be studied using device 10 include, without limitations, nerve cell bodies and tissue culture cells such as smooth muscle, cardiac, and skeletal muscle cells.

Additionally, device 10 can be used, for example, to obtain and measure near field light from nanoscale environment 14. For the purpose of providing a self contained document a description of the near field phenomenon precedes the description of the presently preferred embodiment of the invention.

When light impinges on a boundary surface (such as the surface of nanoscale environment 14) having a varying refractive index at an angle which causes total reflection, the incident light is totally reflected on the boundary surface (reflection plane), in which case the light exudes to the opposite side of the reflection plane. This exuding light is called "near-field light." Other than the foregoing, the near-field light also includes light which exudes from a miniature aperture smaller than the wavelength of the light, through which the light is passed.

The near-field light can be utilized to analyze a surface state (shape, characteristics or the like) of a sample such as semiconductor materials, organic or inorganic materials, vital samples (cells) and the like. An ordinary optical microscope cannot measure a sample at a resolution higher than the wavelength of light due to diffraction of the light. This is called "diffraction limit of light." An analysis-utilizing near-field light permits measurements at a resolution exceeding the diffraction limit of light.

According to a preferred embodiment of the present invention nanowire 12 is adapted to collect near-field light of nanoscale environment 14. As the near-field light incidents on nanowire 12, electronic excitation are induced therein. These electronic excitations cause a current to flow through nanowire 12, toward detection system 16 which detects, records and/or analyzes the current.

It is appreciated that the above embodiments merely exemplify the potential use of device 10 for obtaining vital information from a nanoscale environment, previously unattained by conventional systems and apparati. The geometrical shape, nanometric size and physical properties of nanowire 12 may also be used also for performing tasks, other than, obtaining information.

When two nanostructures encapsulating a conducting material are positioned in closed proximity one to another, a nanometer-scale gap can be formed. Such nanometer-scale gap, also referred to herein as a nanogate, is used in the present invention as a polynucleotide detection gate.

Thus, according to another aspect of the present invention, there is provided an apparatus 11 for characterizing a nucleic acid sequence of a polynucleotide.

Reference is now made to FIGS. 4a-b, which schematically illustrate a top view (FIG. 4a) and a side view (FIG. 4b) of apparatus 11. Apparatus 11 comprises a nanogate 13 defined by two conducting nanowires 12, which, as stated, are formed of a conducting material enclosed by the peptide nanostructures of the present invention. A typical distance between nanowires 12, i.e., a typical width of nanogate 13 is between about 1 nm and 10 nm, inclusive more preferably between about 2 nm and 6 nm, inclusive. Nanowires 12 are preferably formed on a hydrophilic and nonconductive (e.g., silicon oxide) surface 15.

Apparatus 11 further comprises a positioning device 17, for positioning the polynucleotide 19 within nanogate 13. As further detailed hereinunder, in one embodiment, positioning device 17 comprises an arrangement of electrodes 9 designed and constructed to generate an electric field capable of inducing electrophoresis forces on polynucleotide 19.

A controlled thin layer of water or other liquid on surface 15 facilitates the loading and delivery of polynucleotide 19 through the nanogate 13. The width of nanogate 13 (1-10 nm) is sufficient for passage of a single polynucleotide. One ordinarily skilled in the art would appreciate that the specific requirement for nanogate width is also dependent on the temperature and solvent conditions such as the pH and ionic strength of the water or the liquid layer.

When the distance between nanowires 12 is within the above range, significant electron tunneling across the nanogate 13 is generated with application of a tunneling biased voltage thereon. In an aqueous solution (e.g., water), the width of a single-stranded DNA molecule is about 2-3 nm (including some bound water molecules), while that of a double-stranded DNA is about 3-4 nm. Thus, the above preferred ranges for the width of nanogate are sufficient for the passage of either type of DNA chain, and for detection by tunneling current measurement.

The thickness of the adsorbed water or liquid layer increases with increasing humidity. By controlling the relative humidity, the thickness of the water, layer can be manipulated. In addition, by using specific types of surfaces or chemically modified ones, the water adsorption, and thus the thickness of the water layer, can be enhanced. It is possible to maintain a water layer with a thickness that is comparable to that of a single- or double-stranded DNA molecule.

When a nucleic acid sample is loaded into apparatus 11 (e.g., using a micro- or nano-fluidic injection device, not shown), positioning device 17 delivers polynucleotide 19 to nanogate 13, for example, by a pair of electrodes 9.

A precise control of the locomotion of polynucleotide 19 is achieved through the use of electric fields in conjunction with the water or liquid layer. According to a preferred embodiment of the present invention, two electric fields are generated by positioning device 17. The first such field is preferably parallel to surface 15. This field, preferably controlled by electrodes 9, is selected so as to induce electrophoresis forces on polynucleotide 19 in a direction which is parallel to surface 15.

The second electric field is preferably perpendicular to surface 15. This field serves for holding polynucleotide 19 in place and is preferably applied using two planar electrodes 21, located above and beneath surface 15 (sees FIG. 4b).

Thus, the step size of polynucleotide 19 in movement on surface 15 and through nanogate 13 is controlled by the direction, magnitude and duration of the parallel electric field in conjunction with the perpendicular electric field. According to a preferred embodiment of the present invention these two electric fields and the process of molecular characterization are synchronized and coordinated to minimize the time spent by polynucleotide 19 in device apparatus 11. To provide an efficient characterization process, when polynucleotide 19 enters nanogate 13 the parallel electric field is preferably temporarily terminated until the characterization process is completed.

With the perpendicular electric field at the proper magnitude and direction, polynucleotide 19 remains in its location in nanogate 13. For example, for a single-stranded DNA molecule, the perpendicular electric field is preferably directed upwards, so that the (negatively charged) phosphate groups of the DNA molecule are pulled down on surface 15, while its nucleotides pointing upward as desired for base detection. An additional advantage of the use of perpendicular electric field is that this filed prevents any potential drift polynucleotide 19.

When the characterization process is completed, the parallel electric field is generated again so as to remove polynucleotide 19 from gate 13 and to guide another polynucleotide into gate 13.

The characterization process of polynucleotide, 19 using nanogate 13 is known in the art (to this end see, e.g., U.S. Patent Application 20030141189, the contents of which are hereby incorporated by reference). For example, one method is by measuring tunneling current across nanogate 13. Since the chemical compositions and structures of the nucleotides are different, the screening effect of each distinct nucleotide on the tunneling current and other tunneling parameters is different. Representative examples of tunneling parameters, beside the tunneling current, include, without limitation, tunneling I-V curve and/or tunneling dI/dV-V curve, where I represent the tunneling current V represent the tunneling voltage and dI/dV represent the tunneling current slope (first derivative).

Thus, by detecting the difference in the tunneling parameters polynucleotide passing through nanogate 13, the nucleic acid sequence of the polynucleotide can be determined. Using some DNA molecules of known sequence, apparatus 11 can be calibrated, so as to establish a unique tunneling characteristic profile for each distinct DNA base. This tunneling profile is then used as a fingerprint to identify an individual base. With the ability to move polynucleotide 19 through nanogate 13 in a well-controlled manner, reliable sequence information can therefore be obtained at a speed much faster than the current DNA sequencing technology. Since the tunneling electrons likely emerge from a single (or a few) atom(s) of one nanowire, and tunnel through the nanogate 13 to the tip of the other nanowire for the shortest possible distance, the size of the tunneling electron beam is likely to be within a few angstroms (a fraction of a nanometer). This is sufficiently fine to make precise detection of an individual nucleotide of the DNA molecule possible. Therefore, the tunneling detection method can offer a better resolution than that of atomic force microscopy (AFM) probing, described below. The tunneling current method should be able to perform DNA sequencing on either single-stranded or double-stranded DNA, molecules.

Other methods of nucleic acid sequence characterization which are contemplated are, dielectric constant measurements, atomic force microscopy (AFM) or electrostatic force microscopy (EFM) probing.

When the tips of nanowires 12 are placed in close proximity to each other, they can act as elements of a parallel plate capacitor. An alternating voltage (AC voltage) applied between the nanowires 12 in characterized by a phase lag of 90° between the applied voltage and measured current. When a dielectric material such as a nucleic acid molecule is present between the nanowires, the phase lag varies as a function of the dielectric constant of the dielectric material. Thus, according to a preferred embodiment of the present invention, the nucleic acid sequence characterization is done by measuring the dielectric constant of polynucleotide.

The capacitance of the parallel plate capacitor depends on the dielectric constant of the nucleotides and the liquid that are between nanowires 12. For example, the four DNA nucleotides (thymine, adenine, cytosine and guanine) have different structures and compositions, hence also different dielectric constants. When the DNA molecule is positioned in water, the interaction between the DNA and the water molecules also contributes to differences in dielectric constant. Some water molecules are bound or semi-bound around the DNA chain thus less freedom for rotation and are thus less polarizable than the free water molecules in a bulky phase. Consequently, the dielectric constant of the bound or semi-bound water molecules is significantly smaller than that of free water molecules. Since each of the nucleotides has a somewhat different orientation and spatial relation with the phosphate chain, the geometry of the bound or semi-bound water molecules around each distinct nucleotide is also somewhat distinct. This distinct geometry can confer different dielectric constants for each base.

The dielectric constant can be determined by measuring by measuring the phase shift between the input AC voltage and an output voltage signal. Knowing the phase shift, the input and output voltages and the AC frequency, the capacitance, hence also the dielectric constant of polynucleotide 19 can be determined.

By using some DNA molecules of known sequence, calibration of the dielectric constant measurement is possible. A unique phase-shift profile can be established for each distinct DNA base. This profile can be used as a fingerprint to identify an individual base.

Nanostructure generated in accordance with the teachings of the present invention can also be utilized as part of a field emitting device.

Hence, according to another aspect of the present invention, there is provided a field emitter device, which is referred to herein as device 20.

Reference is now made to FIG. 5a, which is a schematic illustration of a cross sectional view of device 20, according to a preferred embodiment of the present invention. Device 20 preferably comprises an electrode 22 and a nanowire 12. Electrode 22 and nanowire 12 are designed and constructed such that when an electrical field is formed therebetween, electrons 27 are extracted from nanowire 12 by tunneling through the surface potential barrier. Once emitted from nanowire 12, electrons 27 can be accelerated, redirected and focused so as to energetically excite atoms of a specific material, as further detailed hereinunder.

Device 20 may be integrated in many apparati, such as, but not limited to, a field emitter display. In this embodiment, a plurality of nanostructures may be positioned in cross points 28 of a matrix 29 of electrodes. Matrix 29, better illustrated in FIG. 5b, is formed of a plurality of row and column electrodes. Thus, each cross point 28 can be addressed by signaling the respective row and column electrodes. Upon a suitable signal, addressed to a specific cross point, the respective bundle of nanostructures 12 emits electrons, in accordance with the above principle.

Device 20 (or the apparatus in which device 20 is employed) may further comprise a substrate 26 having a fluorescent powder coating, capable of emitting light upon activation by the electrons. The fluorescent powder coating may be either monochromatic or multichromatic. Multichromatic fluorescent powder may be, for example, such that is capable of emitting red, green and blue light, so that the combination of these colors provides the viewer with a color image. Device 20 may further comprise a focusing element 25 for ensuring that electrons 27 strike electrode 22 at a predetermined location.

A special use of field emitter device, such as device 20, is in the area of electron beam lithography, in particular when it is desired to achieve a precise critical dimension of order of a few tens of nanometers. The present invention successfully provides an apparatus for electron emission lithography apparatus, generally referred to herein as apparatus 30. As further detailed hereinbelow, apparatus 30 is capable of transferring a pattern of a mask in a nanoscale resolution.

Reference is now made to FIG. 6; which, is a schematic illustration of apparatus 30. Apparatus 30 comprises an electron emission source 32 and an electrically conducting mounting device 34. According to a preferred embodiment of the present invention, sources 32 includes one or more nanostructures 12, which, as stated, is composed of a plurality of peptides. Source 32 and mounting device 34 are kept at a potential difference, e.g., via a voltage source 36. The potential difference is selected such that electrons are emitted from source 32 (similarly to device 20).

A sample 38, on which an e-beam resist 39 to be patterned is formed, is disposed on mounting device 34, in a predetermined distance apart from a source 32. The electrons emitted from nanowire 12 perform a lithography process on a sample 38 mounted thereon. Subsequently, if a developing process is performed, portions of resist 39 which were exposed to the emitted electrons remain when the resist 39 is negative, while portions of resist 39 not exposed to an electron beam remain when resist 39 is positive.

Source 32 and mounting device 34 are preferably positioned in a magnetic field generated by a magnetic field generator 37. Magnetic field generator 37 is designed to precisely control a magnetic field according to the distance between nanostructures 12 and resist 39, so that the electrons emitted from nanowire 12 reach the desired positions on resist 39. Being charged particles moving in a magnetic field, the electrons are subjected to a magnetic force, perpendicular to their direction of motion (and to the direction of the magnetic field vector). Thus, a track of the movement of the electrons is controlled by magnetic field generator 37, which redirect the electron to the desirable position.

Consequently, the shape of nanostructures 12 can be projected upon sample 38, to thereby perform a lithographic process thereon. As described above, according to the present invention, since nanostructures 12 are used as electron emission sources, a lithography process can be performed with a precise critical dimension. In addition, since electrons emitted from nanostructures 12 carbon depreciate portions of resist 39 corresponding to nanowire 12, a deviation between the center of a substrate and the edge thereof are substantially prevented.

An additional use of nanowire 12 is in the field of information storage and retrieving. In certain embodiments, further detailed hereinunder, switching may be achieved based on the observation that the conductance of semiconducting nanowires can change significantly upon either a gate or bias voltage pulse when the surface of the nanowires are appropriately modified, for example, with molecules, functional groups or nanocrystals. Other properties of the nanowire may also be used to record memory, for example, but not limited to, the redox state of the nanowire, mechanical changes, magnetic changes, induction from a nearby field source, and the like.

Specifically, with respect to changes in conductance, subjection to positive or negative gate or bias voltage pulses may cause the change of charge states in the molecules or nanocrystals, and induces the device to make a fully reversible transition between low and high resistance states. The different states may hysterically persist in the set state, even after the voltage source is deactivated. This feature (change in electrical properties upon voltage pulse) may enable the fabrication of electrically erasable and rewritable memory switching devices in which the reversible states are indicated by the conductance of the nanowires. In addition, the memory switching devices may be assembled specifically from nanoscale material building blocks, and may not be created in planar materials by lithography.

Reference is now made to FIGS. 7a-b, which are schematic illustration of a memory cell, generally referred to herein as cell 40. In its simplest configuration, cell 40 comprises an electrode 42 and a nanowire 12. Nanowire 12 preferably capable of assuming one of at least two states. For example, as already described hereinabove, nanowire 12 has the capability to deflect when the Euler buckling force is exceed, thus, a first state of nanowire 12 can be a non-deflected state (when an external force applied on nanostructure 12 is below Euler buckling force) and a second state of nanowire 12 can be a deflected state (when the external force is above or equals the Euler buckling force).

Nanowire 12 is preferably be suspended by one or more supports 44 over electrode 42. Nanowire 12 may be held in position on support(s) 44 in more than one way. For example, nanowire 12 is held in position on support(s) 44 by or any other means, such as, but not limited to, by anchoring nanowire 12 to support(s) 44. The holding of nanowire 12 in its place on support(s) 44 can also be facilitated by chemical interactions between nanowire 12 and support(s) 44, including, without limitation, covalent bonding.

Electrode 42, nanowire 12 and the distance therebetween are preferably selected such that electrical current flows through electrode 42 and/or nanowire 12, generates an electric force on nanowire 12 which is larger than the Euler buckling force. Thus, temporarily electric current(s) transform nanowire 12 from the first state (FIG. 7a) to the second state (FIG. 7b).

A plurality of cells like cell 40 can be incorporated to provide an electromechanical memory array. Each cell in the array can be in either a first state or a second state thus can store a binary information of a first type of datum (say, "0") and a second type of datum (say, "1"). As the size of nanowire 12 is in the nanometric scale, many such cells can be integrated in a single array so that the information storage capacity of the entire array is substantially larger, or at least equivalent to modern memory devices. Each cell may be read or written by applying currents and/or voltages to electrode 42 or nanowire 12.

More specifically, when nanowire 12 is in a non-deflected state (FIG. 7a), cell 40 is characterized by an open circuit, which may be sensed as such on either nanowire 12 or trace electrode 42 when so addressed. When nanowire 12 is in a deflected state (FIG. 7b), cell 40 is characterized by a rectified junction (e.g., Schottky or PN), which may be sensed as such on either nanowire 12 or trace electrode 42 when so addressed.

As will be appreciated by one ordinarily skilled in the art, cell 40 (and therefore an integrated array of a plurality of such cells) is characterized by a high ratio of resistance between "0" and "1" states. Switching between these states is accomplished by the application of specific voltages across nanowire 12 or electrode 42. For example, "readout current" can be applied so that the voltage across a respective junction is determined with a "sense amplifier." It will be appreciated that such reads are non-destructive. More specifically, unlike DRAM systems, where write-back operations are required after each read, cell 40 retains its state even once read is performed.

As stated, the nanostructure of the present invention can also encapsulate a magnetic material, hence to form a magnetic nanowire. A plurality of such magnetic nanowires can be used as a memory cell, which operates according to magnetic principles.

Reference is now made to FIG. 8, which is a schematic illustration of a memory cell, generally referred to herein as cell 60. Cell 60 comprises a plurality of nanowires 12, each formed of a ferromagnetic material enclosed by a peptide nanostructure, as further detailed herein above. Nanowires 12 are capable of assuming two magnetization states. One magnetization state (designated $M_1$ in FIG. 8) may be defined, for example, when the magnetization vector, M, is substantially parallel to a longitudinal axis 62 of nanowires 12 and another magnetization state (designated $M_2$ in FIG. 8) may be when the magnetization vector has a non-negligible angle (say, above 10°) with respect to axis 62.

Thus, binary information can be stored by the two magnetization states of nanowires 12. For example, state $M_1$ can be defined as "0" and state $M_2$ can be defined as "1". One ordinarily skilled in the art would appreciate that well separated magnetization states, also known as a magnetization jump, can be obtained and reproduced precisely from one nanowire to the other by working with nanowires of ferromagnetic materials. The jump from one magnetization state to the other is preferably identified by sweeping an external magnetic field, so that when its magnitude is below a proper threshold, characteristic to the ferromagnetic material and structure of nanowires 12, nanowires 12 assumes the first magnetization state and when the magnitude of the external magnetic field magnitude is above the characteristic threshold, nanowires 12 assumes the second magnetization state.

Cell 60 further comprises a plurality of conductive lines 63, preferably arranged on opposite sides of a membrane 65, such that each nanowire of plurality of nanowires 12 is connected to two conductive lines of plurality of conductive lines 63. This allows for a unique address, represented by a pair of gridwise numbers, to be assigned to each individual nanowire. For example, referring to FIG. 8, nanowire 12a, which is connected to conductive lines 63i and 63j is represented by the address (63i, 63j).

The operation of cell 60 is based upon a physical effect known as the anisotropic magnetoresistance effect, according to which a component of the electrical resistance of a magnetic element varies with a change in the magnetization orientation, of the element and the sensing current flowing therethrough. The change in the electrical resistance depends on the angle between the magnetization vector and the electrical current.

Specific methods of writing and reading information into and out of cell 60 can be found, for example, in U.S. Pat. No. 6,172,902 the contents of which are hereby incorporated by reference.

Generally, the writing processes to a given address, say, address (63i, 63j), is preferably done by injecting a pulsed current into the respective pair of conductive lines, when the magnitude of the external magnetic field is lower by an amount of $\Delta H$ than the characteristic threshold $H_s$. The result of the pulse is to induce the jump from the magnetic state "0" to state "1". The reading process at a given address is preferably done by injecting a current and measuring the potential between the respective pair of conductive lines at a value of the external magnetic field which is between $H_s$-$\Delta H$ and $H_s$. Due to the magnetoresistive property of nanowire 12, the value of the electric potential is shifted.

According to another aspect of the present invention, there is provided an electronic device, for switching, inverting or amplifying, generally referred to as device 50.

Reference is now made to FIG. 9a, which is a schematic illustration of device 50. Device 50 comprises a source electrode 52, a drain electrode 54, a gate electrode 56 and a channel 58. One or both of gate electrode 56 and channel 58 may be formed of a semiconducting material enclosed by a nanostructure which is composed of a plurality of peptides, as further detailed hereinabove. For example, in one embodiment channel 58 is a nanostructure and gate electrode 56 is preferably layer of $SiO_2$ in a silicon wafer.

In its simplest principle, device 50 operates as a transistor. Channel 58 has semiconducting properties (either n-type or p-type semiconducting properties) such that the density of charge carriers can be varied. A voltage 57 is applied to channel 58 through gate electrode 56, which is preferably separated from channel 58 by an insulating layer 59. When the voltage of gate electrode 56 is zero, channel 58 does not contain any free charge carriers and is essentially an insulator. As voltage 57 is increased, the electric field caused thereby attracts electrons (or more generally, charge carriers) from source electrode 52 and drain electrode 54, so that channel 58 becomes conducting.

Thus, device 50 serves as an amplifier or a switching device where, voltage 57 of gate electrode 56 controls the current flowing from source electrode 52 and drain electrode 54, when a bias voltage 53 is applied therebetween.

Two devices like devices 50 may be combined so as to construct an inverter. Referring to FIG. 9b, in this embodiment, a first such device (designated 50a) may include a channel, having an n-type semiconducting properties and a second such device (designated 50b) may include a channel having an p-type semiconducting properties. Devices 50a and 50b are preferably connected such that when bias voltage 53 is applied between the source of device 50a and the drain of device 50b, the combined device serves as an inverter between input signal 51 and output signal 55.

An additional configuration which includes semiconducting nanowire is illustrated in FIG. 10a. In this embodiment, two nanowires 12 forming a junction 92 can serve as a transistor 90. Preferably, the semiconducting material of one of the two nanowires has an n-type doping and the semiconducting material of the other nanowire has a p-type doping.

In accordance with the present invention, one or both of nanowires 12 of transistor 90, has a modulation-doped semiconductor material. This may be achieved by providing a nanowire having either Lewis acid functional groups or Lewis base functional groups to create a region of modulation doping in the junction. One of nanowires 12 comprises the source and the drain portions of transistor 90 and the other nanowire induces the gate function at junction 92. Both pnp and npn transistors that are analogous to bipolar transistors may be formed in this fashion.

Several junctions like junction 92 can be allocated to form a crossbar array 94, which can be used for signal routing and communications between two layers of nanowires. According to the presently preferred embodiment of the invention crossbar array 94 comprises a two-dimensional array of a plurality of junctions similar to junction 92. Each junction servers as a switch which can be either singly configurable or reconfigurable and self-assembling. In one embodiment, at least one of the junctions is a quantum state molecular switch having an electrically adjustable tunnel junction between the respective two nanowires. The switches, formed at each junction, can be electrochemically oxidized or reduced. Oxidation or reduction of the molecule forms the basis of a switch. Oxidation or reduction affects the tunneling distance or the tunneling barrier height between the two nanowires, thereby exponentially altering the rate of charge transport across the junction.

Reference is now made to FIG. 10b which is a simplified illustration of array 94. Array 94 comprises a plurality of junctions 92 defined when two nanowires 12 are crossed at some non-zero angle. Nanowires 12 can be formed of a conducting or semiconducting material enclosed by a peptide nanotube, as further detailed hereinabove. When an appropriate voltage is applied across the nanowires, molecules of each of the two nanowires at the junction point are either oxidized or reduced. When a molecule of one nanowire is oxidized, then a molecule of the other nanowire is reduced so that charge is balanced. These two species are referred to herein as a redox pair.

Distinct electrical circuits 96a and 96b and 96c may be created in array 94 as part of an integrated circuit. Circuits 96a, 96b and 96c can cross each other without being electrically connected where switches, shown as open circles in FIG. 10b and designated 98a, are open. Alternatively, nanowires may be electrically connected by a closed switch, shown as a filled circle in FIG. 10b and designated 98b. By using the voltage across the electrochemical cell formed by each pair of crossed nanowires to make and break electrical connections both along nanowires in a layer (segmented wires) and between wires in two layers (vias), one can create an integrated circuit of arbitrarily complex topology. The wires may connect to an external or an internal electronic device (not shown), e.g., a resonant tunneling diode or a transistor.

This freedom to select a mixture of device types and interconnect topologies includes the possibility that nanowires 12 are heterogeneous in their composition or functionalization. The nanowires in a given layer can be separately formed and functionalized in a plurality of different ways, and subsequently assembled to form a layer that is heterogeneous in nanowire type.

The conducting nanowires of the present invention can also serve as conducting interconnects for electronic circuit assembly of multiple layers. Multi-layered electronic assemblies are used to interconnect a large number of circuit layers. A typical multi-layered assembly has several layers of signal lines, separated by interleaving dielectric layers, and via connections running through one or more dielectric layers perpendicular to the layers surface, as required by the specific electric interconnect network of the assembly.

Reference is now made to FIG. 11, which is a simplified illustration of an electronic circuit assembly 100, according to a preferred embodiment of the present invention. Assembly 100 comprises conductive lines 102 being arranged in at least two layers 104 separated therebetween by a dielectric layer 106. Several conductive lines 102 are electrically connected via one or more conductive nanowire. 12. Nanowires 12 preferably serve as passive conductors for facilitating electrical communication between different layers of assembly 100.

As used herein, the phrase passive conductor referrers to a conductor capable solely to transmit electrical current therethrough.

As used herein, the phrase dynamical conductor referrers to a conductor capable of having to states a transmissive state in which the conductor serve as a passive conductor and a non-transmissive state in which no electrical current is transmitted therethrough.

It will be appreciated that assembly 100 can be combined also with array 94 or several elements thereof, so that nanowires 12 can also be used dynamically. For example, some nanowire can serve mealy as vertically conductive lines between different layers (passive conductors), while other nanowires may form one or more junctions, similar to junction 92, thus allowing switching (dynamic conductors) as further detailed hereinabove.

An additional application in which the nanowires of the present invention can used is in a device for detecting a position and/or movement of an object. Position sensors are used in a variety of modern devices and transducers, for example, in applications for robotics and computer hardware. In robotics, such sensors provide useful information about the state of contact between a robot hand and an object in prehension. In computer-related products such sensors are employed in device such as, but not limited to, mouse, joystick and the like, which respond to movement in two dimensions.

Reference is now made to FIG. 12a, which is a simplified illustration of a device for detecting a position and/or movement of an object, generally referred to herein as device 120. Device 120 comprises a plurality of non-intersecting nanowires 12, formed of conducting or magnetic material enclosed by the peptide nanostructure of the present invention. Nanowires 12 are connected to an electronic circuitry 122, which may have a flat surface or a macroscopically non-flat surface, e.g., a robot's finger tips. The connection between nanowires 12 and circuitry 122 may be via an array of contact pads 124. Each contact pad may be allocated with more than one nanowire so as to form a bundle of nanowires.

FIG. 12b is a schematic illustration of device 120 when contacted by an object 126. Three nanowires are shown in FIG. 12b, designated 12a, 12b and 12c. In operational mode, object 126 contacts nanowire 12a and elastically bends it so that nanowire 12a intersects nanowire 12b which is adjacent thereto. An electrical connection 128 between nanowire 12a and nanowire 12b is thus made possible. Similarly, when objects 126 continues to move, other intersections occur (e.g., between nanowires 12b and 12c).

The location at which object 126 contacts device 120 can thus be detected based on the criterion of electrical connection/no-connection between pairs of contact pads. Device 120 is capable of detecting the position, area, direction of movement, and intensity or strength of the tactile contact (the contact of object 126 with device 120). These factors are generally referred to herein as the position and movement activity of object 126. The position and movement activity can be evaluated by interrogating pairs of contact pads to determine whether an electrical connection has been made between adjacent nanowires.

Whether a connection between nanowires 12 has been made can be sensed by sending a current pulse to contact pads 124 and measuring the electrical resistance. The location of the object can be determined quantitatively based on the number of nanowire being electrically connected at any moment. The time sequence at which the electrical connections are effected provides information on the direction of the motion of object 126. Contact pads 124 can be interrogated sequentially or simultaneously to detect the electrical connection.

The intensity of the tactile force on device 120 may be determined in various ways, such as, but not limited to, evaluation of the physical contact resistance between nanowires that are bent and in contact. The value of the electrical resistance between connected depends on the force applied on nanowire 12.

The conducting or semiconducting nanowires of the present invention may also be used in the field of electrophoretic displays. As stated in the background section that follows, electrophoretic displays employ a plurality of electrically charged particles suspended in a fluid. Under the influence of electric field, the charged particles move through the fluid hence locally alter the optical characterstics of the display.

According to an additional aspect of the present invention there is provided a display system, generally referred to herein as system 130.

Reference is now made to FIG. 13 which is a schematic illustration of system 130. System 130 comprises a fluid 132 containing a plurality of nanostructure devices 134, each being formed of a conducting or semiconducting material enclosed by a peptide nanostructure, as further detailed hereinabove.

Nanostructure devices 134 are distinguished from the pigment particles used in prior art electrophoretic displays by their size. Pigment particles are typically of the order of several hundred nanometers in diameter, or larger. Thus, the diameters of even the smaller pigment particles are of the same order as the wavelengths of visible light, which vary from about 400 nm for blue light to about 700 nm for red light. It is well known to those skilled in the art that the light scattering power of particles is approximately proportional to the sixth power of the particle diameter for particles having diameters less than the wavelength of the relevant light.

Thus, isolated nanostructure devices, which are much smaller than the typical wavelength of light do not appreciably scatter the light and, as such, are effectively transparent. However, the nanostructure devices, when brought into proximity with one another and thus aggregated into larger clusters having diameters comparable to the wavelength of light, scatter light strongly. Thus, by controlling the aggregation level of nanostructure devices 134, one can determine whether the nanostructure devices 134 appear transparent or turbid.

System 130 further comprises an electric field generator 136 capable of generating an electric field effective in shifting nanostructure devices 134 between a dispersed state, corresponding to a first optical characteristic and an aggregated state corresponding to a second optical characteristic.

Conducting nanostructure devices, such as peptide nanostructure encapsulating silver or gold, change color with aggregation. This color change is due to the change in the average refractive index as the aggregates form. When conducting nanostructure devices aggregate, both the color and the intensity of light scattering increases. In other words, the first and second optical characteristics of the display system comprise different colors. For example dispersions of gold nanostructure devices are typically ruby red, while aggregates of gold nanostructure devices vary in color from purple to blue to black depending on the interparticle distance. Thus, in this embodiment, the color of system 130 can be controlled by controlling the degree of aggregation of nanostructure devices 134.

Semiconducting nanostructure devices have strong particle size dependent colors in both the dispersed and aggregated states. The colors are best and most easily seen in fluorescence, and are due to the size dependent quantization of electronic levels in nanostructure devices 134. The smaller the nanostructure device, the larger the band gap and the shorter the wavelength of the fluorescence. Semiconducting nanostructure devices have fluorescent peaks that vary smoothly from about 400 nm to about 700 nm (red) when the size of the nanostructure device varies from about 1.2 nm to about 11.5 nm.

An additional application in which the peptide nanostructures of the present invention can be useful is in the field of thermoelectricity. Thermoelectric devices are devices that either convert heat directly into electricity or transform electrical energy into pumped thermal power for heating or cooling. Such devices are based on thermoelectric effects involving relations between the flow of heat and of electricity through solid bodies.

The formulation of the thermoelectric effect, also known as the Seebeck effect, is as follows. When an open circuit made of a pair of dissimilar metals is held so that two junctions are kept at different temperatures, a potential difference is produced across the terminals of the open circuit. The potential difference is directly proportional to the temperature difference, and does not depend on the distribution of temperature along the metals between the junctions. The factor of proportionality, referred to in the literature as the relative Seebeck coefficient, generally varies with the level of the temperature at which the temperature difference occurs.

The flip side of the Seebeck effect is known as the Peltier effect. According to the Peltier effect a current driven in a circuit made of dissimilar metals causes the different metals to be at different temperatures. Depending on the direction of current flow, heat could be either removed from a junction to freeze water into ice, or by reversing the current heat can be generated to melt ice. The heat absorbed or created at the junction is proportional to the electrical current, and the proportionality constant is known as the Peltier coefficient. The Peltier effect is caused by the fact that an electrical current is accompanied by a heat current in a homogeneous conductor even at constant temperature. The heat current is interchangeably referred to herein as power, as the two quantities have the same physical dimensions (energy per unit time).

The heat current accompanying the electric current, I, is explained by the different flow velocities of the electrons carrying the electric current. The flow velocities depend on the energies of the conduction electrons. For example, if the flow velocity of electrons having an energy above the Fermi energy is higher than for electrons with a lower energy, the electric current is accompanied by a heat current in the opposite direction (since the electronic charge is negative). In this case the Peltier coefficient is negative. Similar situation occurs in an n-doped semiconductor where the electric current is carried by electrons in conduction-band states. Opposite situation (i.e., electrical and heat currents flowing in parallel direction) occurs for a p-doped semiconductor where the electric current is carried by holes.

The operation of thermoelectric devices is based on the Peltier effect. Generally, thermoelectric devices have thermoelectric materials sandwiched between ceramic plates. When the plates have different temperatures (due to the current flowing therebetween) and the heat at the hot plate is dissipated to the ambient environment, this assembly becomes a cooling unit.

Besides the pumping of heat away from the cold plate, there exists two additional thermal processes, which conflict with the Peltier cooling: Joule heating, originating from the electromotive source generating the electrical current, and heat conduction current, flowing from high to low temperatures. The coefficient-of-performance of the cold plate of a thermoelectric device is defined as the ratio of the power at the cold plate, to the total power of the device. The figure-of-merit of the thermoelectric device is defined as $S^2 \sigma T/\kappa$, where S is the Seebeck coefficient, $\sigma$ is the electrical conductivity, T is the temperature and $\kappa$ is the thermal conductivity of the device. An efficient thermoelectric device is characterized by high coefficient-of-performance and high figure-of-merit.

As the Seebeck coefficient, S, and the electrical conductivity, $\sigma$, are competing quantities, any attempt to increase the Seebeck coefficient, results in a decrement of the electrical conductivity. It is therefore appreciated that in conventional materials, a limit to the figure-of-merit is rapidly obtained. Moreover, for a given thermoelectric device, designed for a specific, application at a specific range of temperatures the power of the cold plate and the coefficient-of-performance reach their maximal values at different currents. Practically in conventional thermoelectric devices the current is compromisingly selected in the range between the maximum efficiency and the maximum cooling power.

Hence, the temperature difference between the hot and the cold plates imposes severe limitations on the efficiency of the device. Moreover, even for low temperature differences, in many applications, especially for cooling of small areas, conventional thermoelectric devices are not capable of pumping the required heat fluxes.

The use of low dimensions in the design of thermoelectric devices, is known to have several advantages: (i) enhanced density of states, due to quantum confinement effects, results in an endearment of the Seebeck coefficient without a reduction in the electrical conductivity; and (ii) boundary scattering of electrons or holes reduces the thermal conductivity more than the electrical conductivity, hence further increases the figure-of-merit.

Being practically a one dimension object, the peptide nanostructure of the present invention can be employed in thermoelectric devices. The thermoelectric devices of the present invention can be used in numerous areas of applications, such as, but not limited to, military, medical, industrial, consumer, scientific/laboratory, electro-optics, computers and telecommunications areas. For example, in communications systems, the thermoelectric devices of the present invention can be used keep power amplifiers of transceivers at operating temperature. In the area, of laser devices and, more particularly, semiconductor laser devices, the thermoelectric devices of the present invention can be used for transporting heat away from small areas, thereby to control the operating temperature of the semiconducting laser device Additionally, the thermoelectric devices of the present invention can be used to stabilize temperature in multiplexed fiberoptics communications systems, where heat generation and thermal management is becoming one of the barriers to further increase clock speeds and decrease feature sizes. Still in addition, the thermoelectric devices of the present invention can be used in microprocessors and digital signal processors, where a very small area of high heat must be removed quickly and efficiently.

Thus, according to a yet additional aspect of the present invention, there is provided a thermoelectric device 140.

Reference is now made to FIG. 14 which is a schematic illustration of device 140. Device 140 comprises a first heat conducting layer 142 and a second heat conducting layer 144, where first 142 and second 144 heat conducting layers are interposed by a plurality of nanowires 12. Nanowires 12 are formed of a thermoelectric material encapsulated by the peptide nanostructure of the present invention, as further detailed hereinabove.

It is recognized that the efficiency of thermoelectric device 140 is increased by decreasing the leg diameter to a size at which quantum confinement effects occur. Thus, by using nanowires 12 of the present invention, the performance efficiency is substantially increased. More specifically, because the charge carrier mobility in nanowires 12 is enhances due to quantum confinement effects present therein, the Seebeck coefficient is increased substantially without a decrease in the conductivity of the device.

According to a preferred embodiment of the present invention there are two branches of nanowires 12, designated 12a and 12b in FIG. 14. Nanowires 12a are connected to layer 142 through an electrically conductive layer 146 and nanowires 12b are connected to layer 142 through an electrically conductive layer 148. Layer 144 is preferably electrically conductive. Layers 146 and 148 have no electrical communication thereamongst, other than the electrical communication through nanowires 12a, nanowires 12b and layer 144. Nanowires 12a and 12b preferably have opposite doping nature. For example nanowires 12a may be p-type semiconductors and nanowires 12b may be n-type semiconductors or vice versa.

When current flows from an electromotive source (not shown), free electrons flow through nanowires 12b from layer 142 to layer 144, and holes flow through nanowires 12a from layer 144 to layer 142. In the following, the operation of the 12b branch of device 140 will be explained. One ordinarily skilled in the art would appreciate that a similar description applies also for the second branch, by reversing the sign of the heat and charge carriers, i.e., by replacing electrons with holes.

In operative mode, layer 142 absorbs heat from the environment. The resulting effect is a heat current flowing antiparallel to the electrical current generated by the electromotive source. In other words, the heat (or a portion thereof) is carried by the electrons flowing through nanowires 12b in the direction of plate 144. During the transition of electrons from plate 142 to nanowire 12b, the electrons receive additional energy, sufficient for moving from the Fermi level of free electrons in plate 142 to the conduction band in nanowires 12b. This energy is taken from layer 142 by annihilating phonons in its lattice. Thus, energy is pumped away from layer 142.

When the electrons of nanowires 12b arrive to layer 144, their kinetic energy is delivered thereto, for example, by producing phonons. Thus, energy, originated from, layer 142 is transferred to layer 144. Subsequently, the heat is dissipated to the environment, for example with the aid of a heat sink.

Reference is now made to FIG. 15, which is a schematic illustration of another thermoelectric device, generally referred to herein as device 150. According to a preferred embodiment of the present invention device 150 comprises several three heat conducting regions. Shown in FIG. 15 are three such regions, designated by numerals 151, 152 and 153. Device 150 further comprises two semiconducting regions 154 and 155, which are connected to regions 151, 152 and 153 via two or more nanowires 12. Nanowires 12 are formed of a conducting or thermoelectric material enclosed by the peptide nanostructure of the present invention, as further detailed hereinabove.

Regions 151 and 153 are connected to electromotive sources (not shown), and provide current through device 150. Semiconducting regions 154 and 155 have opposite doping nature. For example region 154 may be a p-type semiconductor and region 155 may be an n-type semiconductor or vice versa. Region 152 serves as the cold part of device 150, while regions 151 and 153 serve as the hot parts thereof. When current passes from region 151 to region 153 though regions 154 and 155 and through nanowires 12, the Peltier effect causes heat to be transmitted out of region 152. Nanowires 12, connecting semiconducting regions 154 and 155 to cold region 152, form quantum cold points. These cold points provide electron confinement and also phonon discontinuity, which limits vibrational energy transfer via the lattice of the materials and hence limits-heat transfer from regions 154 and 155 to cold region 152. These effects improve cooling efficiency of the thermoelectric cooling device.

It will be appreciated that the elements of device 150 can, in principle; engage a single plane. In other words, all the components of device 150 can be formed in a lateral orientation, at the same relative height above the substrate onto which they are formed. Such a lateral configuration is easier to fabricate than a top down structure in forming the points because the shape can be precisely controlled.

One of the advantages of the present invention is that the principles of devices 140 or 150 may be exploited for many applications. For example, several thermoelectric devices may be arranged to form a thermoelectric system capable of pumping more heat than a single device. Being preferably small sized, many thermoelectric devices can be efficiently packed into a relatively compact thermoelectric system. In addition, one or more thermoelectric devices (e.g., a thermoelectric system) may be integrated on an object, such as, but not limited to, an electronic chip, so as to facilitate heat release therefrom.

According to yet an additional aspect of the present invention, nanowire 12 can also be used for performing mechanical tasks. For example, nanowire 12 can be used for manipulating nanoscale objects. One potential application of the present aspect of the invention is in the area of assembling nanoelectronic circuit (see, e.g., cell 40, cell 60, device 50 and transistor 90 hereinabove) when nanoscale objects are to be precisely located in a predetermined location.

Reference is now made to FIG. 16 which is a schematic illustration of a nanoscale mechanical device 70, which comprises at least one nanowire 12 designed and configured for grabbing and/or manipulating a nanoscale object 74. Nanowire 12 is formed of a conducting material enclosed by the peptide nanostructure of the present invention, as further detailed hereinabove. The operation of device 70 may be achieved, for example, using two nanowires 12, preferably tubular nanowires, mounted on a mounting device 72, whereby nanowires 12 perform a constrained motion to grab object 74.

Mounting device 72 can be, for example, a tip end of an atomic force microscopy cantilever, so that one or both of nanowires 12 can also be utilized as an atomic force microscopy probe. In use, nanowires 12 first scan (e.g., as an atomic force microscopy probe) the region where object 74 is expected, thus confirming the position and shape thereof. This scan me be performed in any method known in the art, such as, but not limited to, using a three-dimensional driving mechanism 78.

The motion of nanowire 12 may be controlled, for example, by a voltage source 76 which generates an electrostatic force between nanowires 12. Thus, by activating voltage source 76 nanowires 12 can close or open on object 74.

Once nanowire 12 grip object 74, which, as stated, has been marked by the atomic force microscopy procedure, mounting device 72 can be moved by three-dimensional driving mechanism 78, to a desired location. Subsequently nanowires 12 are further opened, thus releasing object 74 in its appropriate location. In cases where object 74 fails to separate from nanowires 12, e.g., due to Van der Waals forces between object 74 and nanowires 12, a further voltage can be applied between nanowires 12 and the desired location, so that object 74 is released by an electrostatic attractive force.

It is expected that during the life of this patent many relevant structures of nanometric size will be developed and the scope of the term nanostructure is intended to include all such new technologies a priori.

As used herein the term "about" refers to ±10%.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series" Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishelf and Shiigi (eds), "Selected Methods in Cellular Immunology", W. H. Freeman ad Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Self-assembled Aromatic Peptides Can be Used to Cast Metal Nanowires

Materials and Experimental Procedures

Material—Diphenylalanine peptides were purchases from Bachem (Bubendorf, Switzerland). Fresh stock solutions were prepared by dissolving lyophilized form of the peptides in 1,1,1,3,3,3-Hexafluoro-2-propanol at a concentration of 100 mg/ml. To avoid any pre-aggregation, fresh stock solutions were prepared for each and every experiment.

Transmission Electron microscopy—The peptides stock solutions were diluted to final concentration of 2 mg/ml in double distilled water. Then a 10 µl aliquot of 1 day-aged solution of peptide was placed on 200 mesh copper grid, covered by carbon stabilized Formvar film. After 1 minute, excess fluid was removed. For negative staining experiments, the grid was stained with 2% uranyl acetate in water and after two minutes excess fluid was removed from the grid. Silver-filled nanotubes were imaged without staining. Samples were viewed using a JEOL 1200EX electron microscope operating at 80 kV.

Digestion of the self-assembled structures by Proteinase K—Fresh stock solutions of the L-Phe-L-Phe and D-Phe-D-Phe peptides were diluted to a final concentration of 2 mg/ml. After one day, the peptide solutions were examined for the presence of the self-assembled structures by TEM using negative staining. The self-assembled structures were then incubated with a solution of Proteinase K (20 µg/ml) for 1 hour at 37° C. and examined by TEM under the same experimental procedures.

Casting of metal nanowires—A 90 µl aliquot of nanotubes solution (aged for one day) at a concentration of 2 mg/ml was added to a 10 µl boiling solution of 10 mM $AgNO_3$. Citric acid was then added to reach a final concentration of 0.038% to serves as a reducing agent[20]. The silver-filled nanotubes were then incubated with Proteinase K at a final concentration of 100 µg/ml for 1 hour at 37° C. Following the enzymatic degradation, a 10 µl sample of the reaction solution was placed on TEM greed and analyzed without staining.

Results

TEM analysis of diphenylalanine peptides showed a light shell and a dark center, as observed in FIG. 17, suggesting hollow tubular structures filled with the negative stain, uranyl acetate.

To study whether the tubes are truly hollow and filled with aqueous solution, ionic silver was added to the nanotubes in solution. Energy-dispersive x-ray analysis (EDX) indicated the existence of uranium within the assembled structures (FIG. 18a). HR-TEM visualization followed by EDX analysis indicated that silver nanoparticles were formed within the tubes (FIG. 18b).

Based on these observations, the ability of the nanotubes to serve as mold for casting metal nanowires was addressed (FIG. 19a). The tubes were added to boiling ionic silver solution, and the silver was reduced with citric acid to ensure a more uniform assembly of the silver nanowires [Henglein (1999) J. Phys. Chem. B. 103:9533; Enüstün (1963) J. Am. Chem. Soc. 85:3317]. TEM analysis in the absence of staining clearly indicated the formation of metal assemblies within the majority (i.e., 80-90%) of the tubes (FIG. 19b).

Proteolytic lysis of the peptide mold, by the addition of a Proteinase K enzyme to the silver-filled nanotubes solution, resulted in the attainment of individual silver nanowires of about 20 nm in diameter as determined by TEM (FIGS. 2c-d). The diameter of the nanowires, was significantly smaller than that of the tubes, further suggesting that casting was done inside the tubular structure. The chemical identity of the wire was confirmed by EDX analysis (FIG. 18c).

Example 2

Tubular nanostructures were formed from naphthylalanine-naphthylalanine (Nal-Nal) dipeptides, in accordance with preferred embodiment of the present invention. The Chemical structure of the Nal-Nal dipeptide is schematically shown in FIG. 20.

Fresh stock solutions of Nal-Nal dipeptides were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water, then the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIG. 21 is an electron microscope image of the samples, captured a few minutes after the dilution of the peptide stock into the aqueous solution. As shown, the dipeptides form thin (from several nanometers to a few tens of nanometers in diameter) and elongated (several microns in length) tubular structures.

Example 3

Tubular and planar nanostructures were formed from by four different dipeptides, in accordance with preferred embodiment of the present invention.

The following dipeptides were used: (Pentafluro-Phenylalanine)-(Pentafluro-Phenylalanine), (Iodo-Phenylalanine)-(Iodo-Phenylalanine), (4-Phenyl phenylalanine)-(4-Phenyl phenylalanine) and (P-nitro-Phenylalanine)-(P-nitro-Phenylalanine).

For the first two dipeptides [(Pentafluro-Phenylalanine)-(Pentafluro-Phenylalanine) and (Iodo-Phenylalanine)-(Iodo-Phenylalanine)] fresh stock solutions were prepared by dissolving lyophilized form of the peptides in DMSO at a concentration of 100 mg/mL.

For the third and fourth dipeptides [(4-Phenyl phenylalanine)-(4-Phenyl phenylalanine) and (P-nitro-Phenylalanine)-(P-nitro-Phenylalanine)], fresh stock solutions were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water.

In the case of (P-nitro-Phenylalanine)-(P-nitro-Phenylalanine) the final concentration was 5 mg/mL.

Subsequently, the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIGS. 22A-D are electron microscope images of the four samples, captured a few minutes after the dilution of the peptide stock into the aqueous solution.

FIG. 22A shows tubular assemblies formed by the (Pentafluro-Phenylalanine)-(Pentafluro-Phenylalanine) dipeptide, FIG. 22B shows tubular structures assembled by (Iodo-Phenylalanine)-(Iodo-Phenylalanine), FIG. 22C shows planar nanostructures formed by (4-Phenyl phenylalanine)-(4-Phenyl phenylalanine), and FIG. 22D shows fibrilar assemblies of (P-nitro-Phenylalanine)-(P-nitro-Phenylalanine).

Altogether these results suggest the use of the peptide nanotubes of the present invention for numerous nano-technology applications.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition comprising a metal at least partially enclosed by a discrete tubular, nanostructure composed of a plurality of aromatic homodipeptides.

2. The composition of claim 1, wherein said discrete tubular nanostructure does not exceed 500 nm in diameter.

3. The composition claim 1, wherein said discrete tubular nanostructure is at least 1 nm in length.

4. The composition of claim 1, wherein said plurality of aromatic homodipeptides comprise amino acids selected from the group of naturally occurring amino acids, synthetic amino acids and combinations thereof.

5. The composition of claim 1, wherein said plurality of aromatic homodipeptides comprise D-amino acids.

6. The composition of claim 1, wherein said plurality of aromatic homodipeptides comprise L-amino acids.

7. The composition of claim 1, wherein said discrete tubular nanostructure is stable at a temperature range of 4-200° C.

8. The composition of claim 1, wherein said discrete tubular nanostructure is stable in an acidic environment.

9. The composition of claim 1, wherein the discrete tubular nanostructure is stable in a basic environment.

10. The composition of claim 1, wherein said plurality of aromatic homodipeptides comprise aromatic moieties selected from the group consisting of substituted or unsubstituted naphthalenyl and substituted or unsubstituted phenyl.

11. The composition of claim 10, wherein said substituted phenyl is selected from the group consisting of pentafluoro phenyl, iodophenyl, biphenyl and nitrophenyl.

12. The composition of claim 1, wherein said plurality of aromatic-homodipeptides are selected from the group consisting of naphthylalanine-naphthylalanine dipeptide, (pentafluro-phenylalanine)-(pentafluro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

13. The composition of claim 1, wherein said metal is selected from the group consisting of silver, gold, copper, platinum, nickel and palladium.

14. The composition of claim 1, wherein said plurality of aromatic homodipeptides comprise di-phenylalanine.

* * * * *